(12) United States Patent
Dorier et al.

(10) Patent No.: US 10,457,087 B2
(45) Date of Patent: Oct. 29, 2019

(54) SECURITY ELEMENT FORMED FROM AT LEAST TWO MATERIALS PRESENT IN PARTIALLY OR FULLY OVERLAPPING AREAS, ARTICLES CARRYING THE SECURITY ELEMENT, AND AUTHENTICATION METHODS

(71) Applicant: SICPA HOLDING SA, Prilly (CH)

(72) Inventors: Jean-Luc Dorier, Bussigny (CH); Mia Milos-Schouwink, Vevey (CH); Xavier Cédric Raemy, Belmont-sur-Lausanne (CH)

(73) Assignee: SICPA HOLDING SA, Prilly (CH)

( * ) Notice: Subject to any disclaimer, the term of this patent is extended or adjusted under 35 U.S.C. 154(b) by 0 days.

(21) Appl. No.: 16/063,681

(22) PCT Filed: Dec. 13, 2016

(86) PCT No.: PCT/EP2016/080785
§ 371 (c)(1),
(2) Date: Jun. 18, 2018

(87) PCT Pub. No.: WO2017/102723
PCT Pub. Date: Jun. 22, 2017

(65) Prior Publication Data
US 2019/0126659 A1    May 2, 2019

(30) Foreign Application Priority Data
Dec. 17, 2015 (EP) .................................... 15200955

(51) Int. Cl.
*G06K 7/10* (2006.01)
*B42D 25/378* (2014.01)
(Continued)

(52) U.S. Cl.
CPC ........... *B42D 25/378* (2014.10); *B41M 3/144* (2013.01); *B42D 25/382* (2014.10);
(Continued)

(58) Field of Classification Search
USPC ................ 235/468, 494, 379, 451, 469, 491
See application file for complete search history.

(56) References Cited

U.S. PATENT DOCUMENTS

| 6,309,701 B1 | 10/2001 | Barbera-Guillem |
| 6,808,542 B2 | 10/2004 | Nguyen et al. |

(Continued)

FOREIGN PATENT DOCUMENTS

| DE | 60030730 | 9/2007 |
| WO | 2009002329 | 12/2008 |

(Continued)

OTHER PUBLICATIONS

International Search Report (ISR) and Written Opinion (WO) issued with respect to application No. PCT/EP2016/080785, 14 pages.
(Continued)

*Primary Examiner* — Tuyen K Vo
(74) *Attorney, Agent, or Firm* — Muncy, Geissler, Olds & Lowe, P.C.

(57) ABSTRACT

Security element comprising a first material MAT1 and a second material MAT2 formed in or on a substrate, in such a manner that areas occupied by MAT1 and MAT2 overlap partially or fully,
the first material MAT1 comprising a phosphorescent pigment (donor),
the second material MAT2 comprising a fluorescent dye or pigment (acceptor),
wherein the phosphorescent pigment present in MAT1 is capable of emitting phosphorescence radiation in at least one first phosphorescence emission wavelength range λ1e
(Continued)

upon excitation by electromagnetic radiation falling within a phosphorescence excitation wavelength range $\lambda 1a$, and the fluorescent dye or pigment present in MAT2 is capable of emitting fluorescence radiation in at least one second fluorescence emission wavelength range $\lambda 2e$ upon excitation by electromagnetic radiation falling within an fluorescence excitation wavelength range $\lambda 2a$ of the fluorescent dye or pigment, and said first phosphorescence emission wavelength range $\lambda 1e$ of the phosphorescent pigment present in MAT1 overlaps with the excitation wavelength range $\lambda 2a$ of the fluorescent dye or pigment present in MAT2, so that after irradiation of the security element with electromagnetic radiation within the phosphorescence excitation wavelength range $\lambda 1a$ the emission of fluorescence radiation in the emission wavelength range $\lambda 2e$ is observable.

24 Claims, 15 Drawing Sheets

(51) Int. Cl.
| | | |
|---|---|---|
| G07D 7/12 | (2016.01) | |
| B42D 25/382 | (2014.01) | |
| B42D 25/387 | (2014.01) | |
| B41M 3/14 | (2006.01) | |
| C09D 11/033 | (2014.01) | |
| C09D 11/037 | (2014.01) | |
| C09D 11/101 | (2014.01) | |
| C09D 11/106 | (2014.01) | |
| C09D 11/30 | (2014.01) | |
| C09D 11/50 | (2014.01) | |
| G07D 7/00 | (2016.01) | |
| G07D 7/1205 | (2016.01) | |
| B42D 25/405 | (2014.01) | |
| C09D 11/54 | (2014.01) | |
| G01N 21/64 | (2006.01) | |
| G06K 7/14 | (2006.01) | |
| G06K 19/06 | (2006.01) | |

(52) U.S. Cl.
CPC ......... *B42D 25/387* (2014.10); *B42D 25/405* (2014.10); *C09D 11/033* (2013.01); *C09D 11/037* (2013.01); *C09D 11/101* (2013.01); *C09D 11/106* (2013.01); *C09D 11/30* (2013.01); *C09D 11/50* (2013.01); *C09D 11/54* (2013.01); *G01N 21/6456* (2013.01); *G06K 7/1413* (2013.01); *G06K 7/1417* (2013.01); *G06K 7/1443* (2013.01); *G06K 19/06028* (2013.01); *G06K 19/06037* (2013.01); *G06K 19/06103* (2013.01); *G07D 7/003* (2017.05); *G07D 7/12* (2013.01); *G07D 7/1205* (2017.05); *G07D 2207/00* (2013.01)

(56) References Cited

U.S. PATENT DOCUMENTS

| | | | |
|---|---|---|---|
| 7,079,230 | B1 | 7/2006 | McInerney et al. |
| 8,840,983 | B2* | 9/2014 | Downing ............. G07D 7/1205 428/195.1 |
| 2003/0154647 | A1 | 8/2003 | Nguyen et al. |
| 2006/0237541 | A1* | 10/2006 | Downing ............. G07D 7/1205 235/462.01 |
| 2008/0014378 | A1* | 1/2008 | Hoffmuller ............ B42D 25/29 428/29 |
| 2008/0121815 | A1* | 5/2008 | Agrawal ................... G09F 3/00 250/473.1 |
| 2012/0021251 | A1* | 1/2012 | Agrawal .................. B05D 5/06 428/690 |
| 2013/0147181 | A1* | 6/2013 | Rosset ................... D21H 21/40 283/92 |
| 2014/0065442 | A1* | 3/2014 | Kingsley ............ C09K 11/7792 428/690 |
| 2015/0298482 | A1* | 10/2015 | Walter ................... G02B 5/008 359/572 |

FOREIGN PATENT DOCUMENTS

| | | |
|---|---|---|
| WO | 2009010714 | 1/2009 |
| WO | 2011046642 | 4/2011 |
| WO | 2013033009 | 3/2013 |
| WO | 2013050290 | 4/2013 |
| WO | 2014076049 | 5/2014 |

OTHER PUBLICATIONS

International Preliminary Report on Patentability (IPRP) issued with respect to application No. PCT/EP2016/080785, 22 pages.
D. L. Andrews, A Unified Theory of Radiative and Radiationless Molecular Energy Transfer; Chemical Physics 135 (1989) 195-201.
D.M. Sturmer, The Chemistry of Heterocyclic Compounds, vol. 30, John Wiley, New York, 1977, pp. 441-587.
J.B. Marling, J.H. Hawley, E.M. Liston, W.B. Grant, Applied Optics, 13(10), pp. 2317-2320 (1974).
Persistent Luminescence in Eu2+-Doped Compounds, a Review, Materials, 2010, 3, 2536-2566.
Persistent Luminescence in Non-Eu2+-Doped Compounds, a Review, Materials 2013, 6, 2789-2818.

* cited by examiner

Figure 3b - I
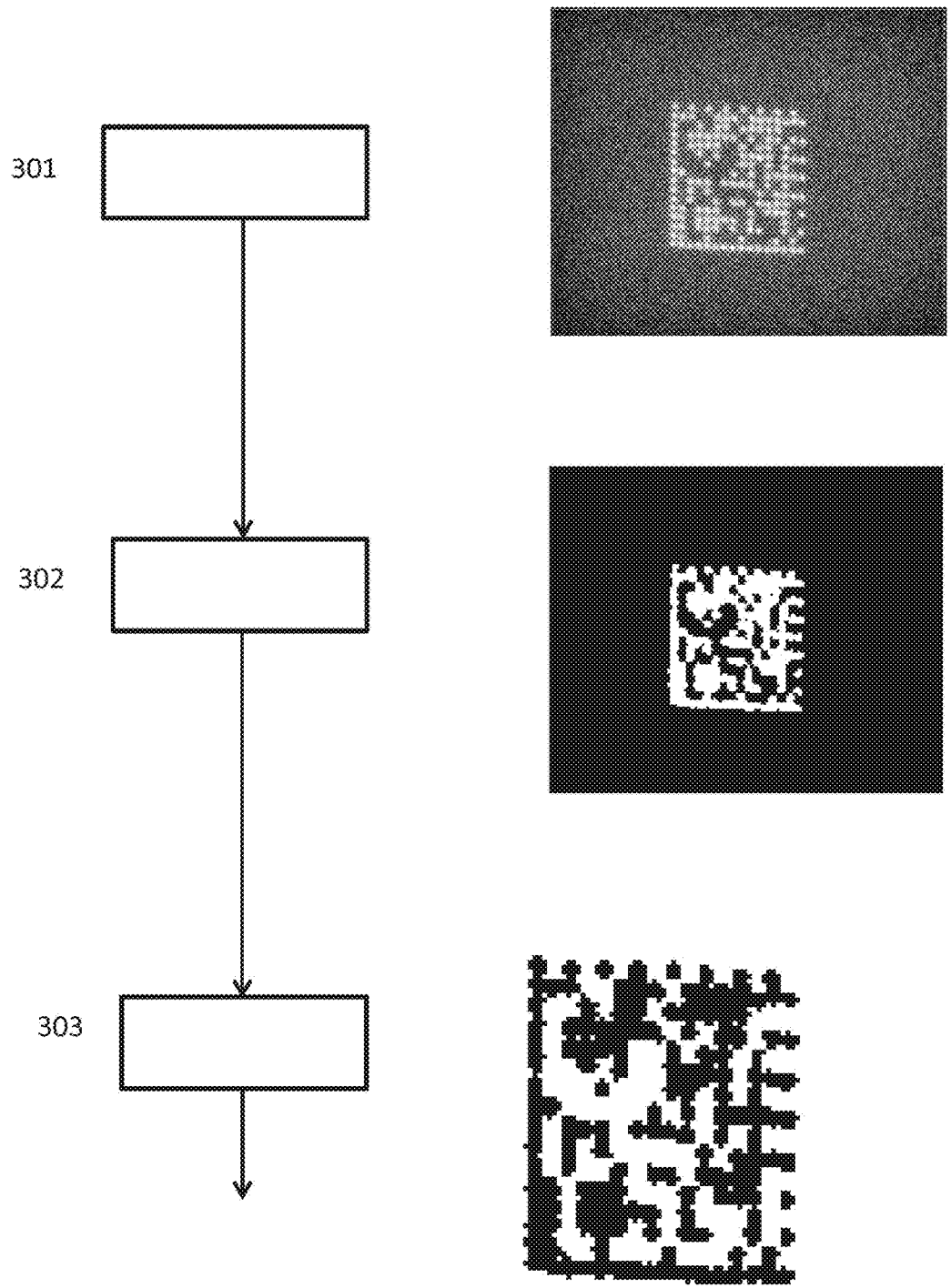

Figure 3b - II
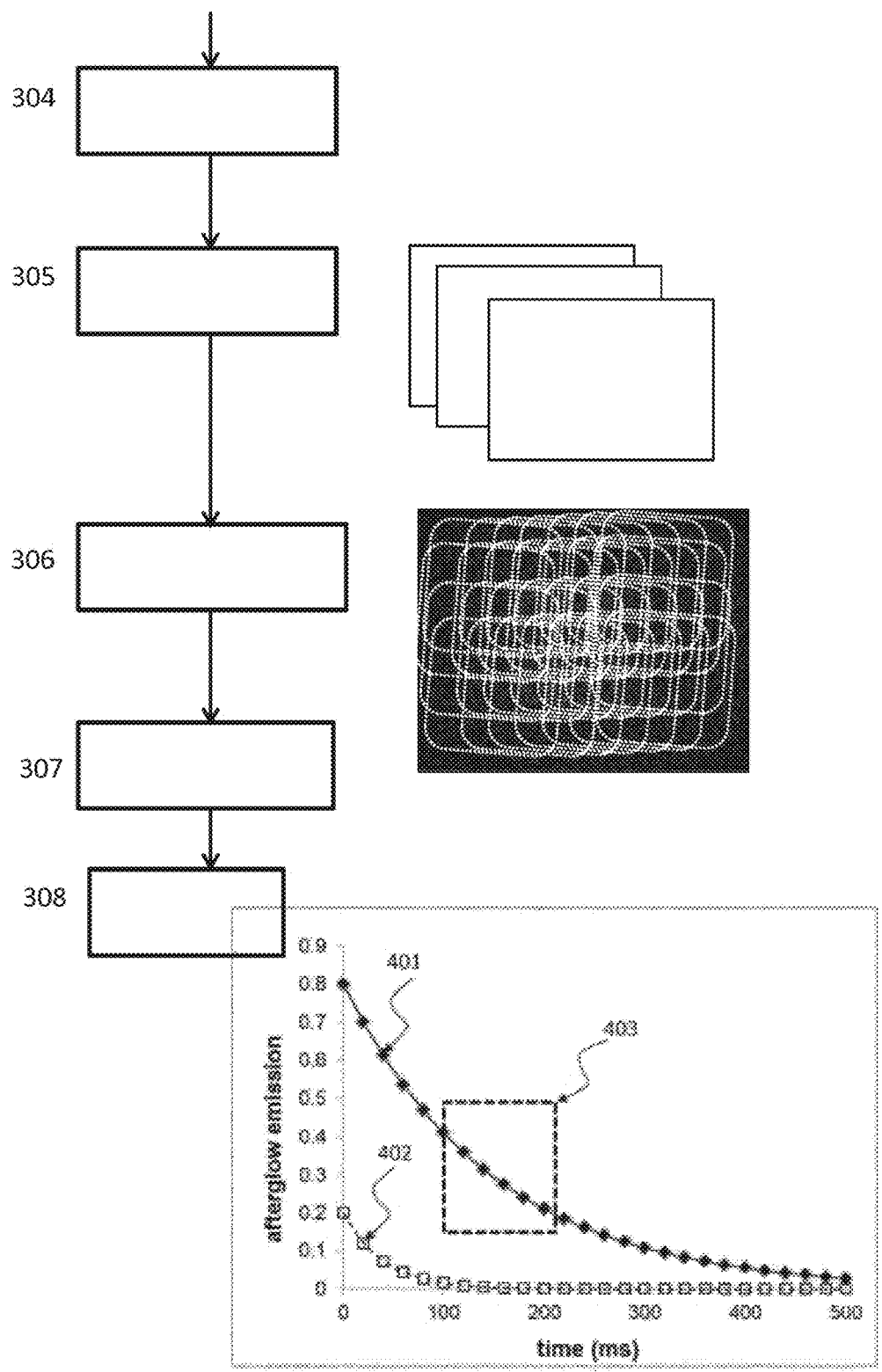

SECURITY ELEMENT FORMED FROM AT LEAST TWO MATERIALS PRESENT IN PARTIALLY OR FULLY OVERLAPPING AREAS, ARTICLES CARRYING THE SECURITY ELEMENT, AND AUTHENTICATION METHODS

BACKGROUND OF THE INVENTION

Security elements are often used to indicate the authenticity and genuineness of various items, including banknotes, member cards, concert tickets, different kinds of commercial goods of value such as perfumes, fashion items or replacement parts for cars and planes, just to mention a few. The use of such security elements is becoming more and more widespread in view of increasing numbers of forged and bogus products, as the security element poses a difficulty to any counterfeiter in the reproduction of bogus products.

Security elements that are based on fluorescence phenomenon are widely used. Fluorescence is observed if a fluorescent material, typically a dye or pigment, is exposed to excitation radiation. It follows a decay of the excited material, causing emission as a wavelength different from the excitation wavelength. The response of the material (i.e. the intensity and/or color of the observed emission in response to the excitation) is indicative for the genuineness of the material protected by the security element. For instance, fluorescent materials are used for security elements present on banknotes, wherein an excitation of 348 nm wavelength causes a fluorescence emission in bright green yellow.

The level of security provided by such fluorescence-only security elements is moderate at the most, as many fluorescent materials are commercially available, and mainly prevents copying on a copying machine. A counterfeiter may thus easily come into possession of a suitable material for mimicking the behavior of an authentic security element. The emission spectra of commercially available markers (dyes or pigments) are well documented and furthermore can be measured by a counterfeiter that suspects them to be used to protect the authenticity of an article. Even if two or more dyes or pigments have been used in combination, e.g. for forming two patterns on a substrate, counterfeiters may purchase these and prepare a corresponding mixture thereof, in order to mimic the security mark of an article.

Further, conventional security elements are mainly produced by printing. The industrial printing technologies currently available for printing e.g. serialized codes include mostly inkjet (Continuous Ink Jet—CIJ or by drop on demand—DoD). The choice of suitable fluorescent products that can be incorporated in the ink formulation for these technologies is limited due to the small size of the printer head nozzles. Mostly soluble organic dyes or fine organic pigments are used to avoid nozzle clogging. These fluorescent products all have very short (nanosecond or shorter) emission lifetimes, which prevent from using the luminescence decay time as an authentication criterion with standard imaging devices such as hand-held devices.

Other authentication methods rely on the decay time of phosphorescent markers. For implementing such authentication method with a standard imager at relatively low frame rate (typically 50 frames per second), the decay time should be relatively long (tens to hundreds of milliseconds). The long afterglow phosphors currently available have coarse pigment particle sizes (>10 microns) which prevent them from being digitally printed. CIJ or DoD printers have tiny nozzles which would be clogged by the phosphor pigments and crushing the pigment particles to smaller sizes lead to a loss of their properties. When codes are printed such that they are not visible to unaided eye, there are even additional limitations on the choice of fluorescent products and more stringent requirements on ink formulation. In summary, current digitally printed secure fluorescent codes are restricted to the use of soluble organic dyes or fine pigments with short and non-specific fluorescence lifetime.

An additional problem with actual methods used for serialization of product with printed secure Dot-matrix codes on pre-printed labels is that the link between the label and the code is not secured. In other words, non-serialized pre-printed labels can be stolen by bad people who could potentially print their own serialization codes for counterfeiting products.

Further, such conventional security elements rely on the use of one species only for forming the security element. Nowadays, however, with the increasing trend of a product being manufactured at different places, there is a need for security elements that can provide a link between different places and different times, e.g. between pre-printed labels and a product code. This allows for providing a means for indicating the authenticity of a product along its chain of manufacture.

A more reliable authentication of luminescent marks with imaging devices can be achieved by exploiting the spectral properties of the emitted light, i.e. by analyzing the emission spectrum in the visible spectrum or in other spectral ranges, such as UV and IR. With a standard imaging sensor, performing multi (or hyper) spectral imaging, e.g. in the NIR (near infrared range) range, would require techniques such as: (1) custom Bayer-like filters (involving expensive developments) (2) Fabry-Perot configurations (currently bulky and fairly expensive), (3) complex cameras using AOTF (Acousto-Optic Tunable Filters, which also bulky and expensive), (4) switchable band-pass interference filters (with inconvenient moving parts), or (5) imaging spectrographs requiring push-brooms (unsuitable for handheld readers). Thus, the finer analysis of spectral properties generally requires complex, bulky and expensive equipment, and is difficult to implement in handheld devices or widely distributed authentication equipment.

Another means to achieve a more reliable authentication is a spectrometer. However, this device does not provide an image of the mark, making it unsuitable for code reading or geometrical checks of the printed mark.

Prior art authentication methods relying on imagers thus mainly rely on the type of emission observed. Yet, the intensity of the emission and/or the time-dependent emission behavior is generally not used for authentication purposes. Put differently, the prior art authentication methods generally check if the expected emitting species is present. Interactions between certain materials other than the emitting species, or interactions between different emitting species, are generally not used for authentication purposes. Also, the chemical surrounding of chemical species is typically not used for authentication purposes.

In addition, for Secure Track and Trace of products and/or for excise tax recovery enforcement of various goods, serialized digital marks (e.g. Dot-matrix or bar-codes) are printed on labels affixed to the products or printed directly onto the products or their packages. In order to prevent from copying or forging these codes, security inks are used. In some applications, fluorescent inks are used to print these codes which are detected and decoded using special readers which aim at measuring the ink luminescence properties for authentication. In some applications it is desired that the Public may also read and decode the security codes, which therefore have to be reflective in the visible spectral range (visible codes). This does not prevent from having secure codes that are visible and fluorescent.

Most of the security code readers are detecting ink luminescence over a relatively broad spectral range and hence are not taking advantage of the full specific luminescence properties (e.g. spectral shape of the emission). To guarantee a certain degree of covertness and further providing resistance to copy, the secured codes are optionally invisible to unaided eye. But in this case they cannot be decoded by the Public, which is a disadvantage for certain applications.

U.S. Pat. No. 7,079,230 B1 relates to authentication devices and methods and, more particularly, to portable hand-held device and a method for authenticating products or product packaging. In one embodiment of this patent document, a method of selecting a light-sensitive compound for application to a substrate and subsequent detection on the substrate is disclosed. The method includes irradiating the substrate with light, sensing an emission spectrum of the substrate in response to the irradiation, determining at least one peak wavelength of light within the emission spectrum, and selecting a light-sensitive compound that emits or absorbs light at a first wavelength in response to the irradiating light wherein the first wavelength is different from the at least one peak wavelength. In another embodiment, a method of authentication is described which includes producing an ink containing a first compound that emits light at a first discreet wavelength and a second compound that emits light at a second discreet wavelength, printing a readable image on a substrate with the ink, detecting a ratio of the first compound with the second compound on the substrate, indicating whether the ratio is within a range and reading the image. In one embodiment, one or more light-sensitive compounds, such as, for example, one or more fluorescent light-emissive compounds, is mixed with ink to be printed on a product or a product package. The system of this reference document requires the measurement of at least two different emission peaks and consequently requires a measuring device that contains two separate detectors, one for each emission peak.

WO 2013/050290 A1 describes a method for the automatic examination of the authenticity of value-indicating stamps and indicia comprising a luminescent area, the stamp or indicium being applied to the surface of a mail item. The surface of the item is irradiated with light of a wavelength of spectral range, a first image of the surface of the item is recorded by means of a camera system and said first image is evaluated with respect to the location of stamps or indicia applied thereto on the surface of the item. A comparison of evaluation of the image sections or image sections with stored luminescence patterns will lead, when these match, to a decision on the authenticity of every stamp or indicium.

While fluorescent dyes are widely used in authentication marks and security elements, the use of pigments, in particular phosphorescent pigments, is limited. Such phosphorescent pigments are often coarse materials that cannot be utilized in many printing applications, such as inkjet printing. Accordingly, their use is limited in practice.

Problems to be Solved by the Present Invention

The present invention thus aims at providing a harder to counterfeit security element. In a separate or additional aspect, the security element should be relatively easy to identify as genuine, preferably not requiring the use of bulky and/or complicated equipment.

The present invention also aims at providing a security element that creates a distinct visual effect observable under certain viewing or illumination conditions.

The present invention further aims in one aspect at expanding the materials possibly to be used in security elements by providing security element features not by fine printing (e.g. inkjet), but by methods that are more tolerable to larger particle sizes.

Further, it would be advantageous if the new security element and its authentication method can be realized at least partially by using printing inks, as this allows the printing of fine designs such as logos and images obtainable by printing inks, including but not limited to inkjet printing, but hardly accessible with other methods.

The invention also aims at providing a highly secure photo-physical link between different materials that may be applied at different places, e.g. different places of manufacture. An example is a pre-printed label or package and a subsequently provided item-specific element, such as a serialization digital code, Barcode or Datamatrix.

In certain embodiments, the present invention further aims at providing a stronger authentication of visible or invisible Dot-Matrix codes, wherein a printed code is securely linked to a printing substrate, such as a label or package, and which can be authenticated without requiring expensive or complex reading device.

In certain embodiments, the present invention aims to provide stronger authentication of visible or invisible Dot matrix codes digitally printed with short lifetime fluorescent organic dye on pre-printed labels without requiring an expensive or complex reading device. Furthermore this marking and authentication method also guarantees a secured link between the Dot-matrix code and the pre-printed label or package.

The present invention furthermore aims at providing a security element whose emission response to excitation radiation depends not only on the type of emitting species present in the security element, but which is also sensitive to the mode of manufacture of the security element and the presence, type and amount of components other than the emitting species, as then a counterfeiter not only needs to identity the emitting species, but also to reverse engineer the entire composition and the manufacturing process in order to mimic an authentic security element.

The present invention furthermore aims at expanding the criteria that can be used for authentication purposes beyond those currently used, such as emission wavelength of a fluorescent material.

SUMMARY OF THE INVENTION

The present invention has been made to achieve some or all of the above aims and provides a novel security element that relies on the interaction of two materials MAT1 and MAT2 as a means for indicating the genuineness of a mark. The materials MAT1 and MAT2 are arranged in or on a substrate (in other words, MAT1 can be arranged within the bulk of the substrate, on one or both surfaces of the substrate, or both within the bulk and on one or both surfaces of the substrate; equally MAT2 can be arranged within the bulk of the substrate, on one or both surfaces of the substrate, or both within the bulk and on one or both surfaces of the substrate) such that the areas occupied by MAT1 and MAT2 overlap partially or fully when viewed perpendicular to the substrate, as in overlapping prints on a sheet of paper or a print on a paper substrate.

MAT1 comprises a phosphorescent pigment whereas MAT2 comprises a fluorescent dye or pigment. In the area of overlap, at least a part of phosphorescence emission of MAT1 is utilized to cause excitation of the fluorescent material present in MAT2, to thereby induce fluorescence emission. In view of MAT1 comprising a phosphorescent material having a longer decay time of the phosphorescent emission as compared to fluorescence, the fluorescence emission from MAT2 can be observed even after the phosphorescence excitation radiation for MAT1 ceased. This allows using also the time-dependent afterglow intensity after ceasing the phosphorescence excitation as a means for determining the genuineness of the security element, thereby expanding the criteria for authentication to a time-dependent domain.

The present invention thus provides the following aspects;

A security element comprising a first material MAT1 and a second material MAT2 formed in or on a substrate, in such a manner that areas occupied by MAT1 and MAT2 overlap partially or fully,
  the first material MAT1 comprising a phosphorescent pigment (donor),
  the second material MAT2 comprising a fluorescent dye or pigment (acceptor),
wherein the phosphorescent pigment present in MAT1 is capable of emitting phosphorescence radiation in at least one first phosphorescence emission wavelength range $\lambda 1e$ upon excitation by electromagnetic radiation falling within a phosphorescence excitation wavelength range $\lambda 1a$, and the fluorescent dye or pigment present in MAT2 is capable of emitting fluorescence radiation in at least one second fluorescence emission wavelength range $\lambda 2e$ upon excitation by electromagnetic radiation falling within an fluorescence excitation wavelength range $\lambda 2a$ of the fluorescent dye or pigment, and
said first phosphorescence emission wavelength range $\lambda 1e$ of the phosphorescent pigment present in MAT1 overlaps with the excitation wavelength range $\lambda 2a$ of the fluorescent dye or pigment present in MAT2, so that after irradiation of the security element with electromagnetic radiation in the phosphorescence excitation wavelength range $\lambda 1a$ the emission of fluorescence radiation in the emission wavelength range $\lambda 2e$ is observable.

The security element may be such that MAT1 is an ink applicable by gravure printing, offset printing, intaglio printing, pad printing, flexographic printing or screen printing, and MAT2 is an ink applicable by inkjet printing, preferably selected from continuous inkjet printing and drop-on-demand inkjet printing or ink spraying.

The security element according to the invention may be provided such that MAT2 forms or is comprised in a digital code, such as a QR code, dot-matrix code or bar code.

The security element may be such that MAT2 forms or is comprised in a serial code or product code, and/or wherein code formed by MAT2 or in which MAT2 is comprised is item-specific, batch-specific or product-specific, preferably item-specific.

The security element may be such that MAT1 and MAT2 are present in the form of layers on a substrate, and MAT2 is provided directly on MAT1, or wherein MAT1 is provided directly on MAT2.

The security element may be such that MAT1 is comprised in the substrate and MAT2 is provided directly on the substrate, or wherein MAT2 is comprised in the substrate and MAT1 is provided directly on the substrate.

The security element may be such that the substrate comprising MAT1 or MAT2 is selected from one or more of glass, ceramics, plastics, paper, and cardboard.

The security element may be such that one or both of MAT1 and MAT2 is/are not visually distinguishable from the substrate by the naked eye.

The security element may be such that one or both of MAT1 and MAT2 is/are provided in the form of a pattern, indicia, symbol or logo.

The security element may be such that MAT1 is provided in the form of a pattern, indicia, symbol or logo, and wherein MAT2 is provided in the form of a code, preferably a digital code, such as a QR code, dot-matrix code or bar code, which may or may not be item-specific, product-specific or batch-specific.

The security element may be such that the area wherein MAT1 is provided entirely includes the area wherein MAT2 is provided.

The security element may be such that $\lambda 1a\text{-max}<\lambda 1e\text{-max}<\lambda 2e\text{-max}$, wherein $\lambda 1a\text{-max}$, $\lambda 1e\text{-max}$, and $\lambda 2e\text{-max}$ denote the wavelengths of the excitation and emission peaks in the respective excitation and emission wavelength regions of the phosphorescent pigment present in MAT1 and the fluorescent dye or pigment present in MAT2.

The invention also relates to a method for authenticating a security element as described above, which comprises the steps
  i. irradiating the security element with a light source in the wavelength range $\lambda 1a$ for a given time to excite the phosphorescent pigment in MAT1 to emit phosphorescence radiation in the wavelength range $\lambda 1e$;
  ii. after the given time has elapsed, subsequently detecting a response emitted by a region of a spatial overlap of the security element within the wavelength range $\lambda_{2e}$, and
  iii. judging the authenticity of the security element on the basis of the response in the wavelength range $\lambda_{2e}$.

The authentication method may be such that step iii. comprises a sub-step iii.a of extracting a value related to at least one parameter associated with the emission in the wavelength region $\lambda_{2e}$ and a sub-step iii.b of determining whether the extracted value corresponds within a certain level of confidence to a value that is characteristic for an authentic security element.

The authentication method may be such that the parameter is associated with the intensity of the observed emission in the wavelength region $\lambda_{2e}$.

The authentication method may be such that the parameter is associated with the decay time of the phosphorescent pigment.

The authentication method may be such that the method additionally comprises steps for acquiring an image of the security element in the wavelength range $\lambda_{2e}$ upon illumination in the wavelength range $\lambda_{2a}$, and processing the acquired image.

The invention also relates to a method as described, which further comprises generating a digital correlation mask from said image.

The invention also relates to an authentication apparatus for authenticating the security element as described above in accordance with a method as described above, the apparatus comprising a radiation source for performing step i, a detector for performing step ii and a processing unit for performing step iii.

The authentication apparatus may be such that it comprises a first radiation source for emitting substantially in the wavelength range λ1a for irradiating the phosphorescent pigment in MAT1;

an imager selectively sensitive in the wavelength range λ2e for capturing images of the security element;

a computing device for storing and processing the captured images under the first radiation source and for comparing the processed image result with a set of pre-defined stored rules to judge whether the security element is authentic.

The authentication apparatus may be such that it further comprises a second light source emitting substantially in the wavelength range λ2a for irradiating the fluorescent dye or pigment in MAT2.

The authentication apparatus may be such that said computing device is furthermore arranged for decoding information in a digital code.

The invention also relates to a commercial good of value or security document comprising the security element as described above.

The invention also relates to a process for producing a security element as described above, which comprises providing a first material MAT1 and a second material MAT2 in or on a substrate, in such a manner that the areas occupied by MAT1 and MAT2 overlap fully or partially, the first material MAT1 comprising a phosphorescent pigment (donor), the second material MAT2 comprising a fluorescent dye or pigment (acceptor), wherein the phosphorescent pigment present in MAT1 is capable of emitting phosphorescence radiation in at least one first phosphorescence emission wavelength range λ1e upon excitation by electromagnetic radiation falling within a phosphorescence excitation wavelength range λ1a, and the fluorescent dye or pigment present in MAT2 is capable of emitting fluorescence radiation in at least one second fluorescence emission wavelength range λ2e upon excitation by electromagnetic radiation falling within an fluorescence excitation wavelength range λ2a of the fluorescent dye or pigment, and said first phosphorescence emission wavelength range λ1e of the phosphorescent pigment present in MAT1 overlaps with the excitation wavelength range λ2a of the fluorescent dye or pigment present in MAT2, so that after irradiation of the security element with electromagnetic radiation within the phosphorescence excitation wavelength range λ1a the emission of fluorescence radiation in the emission wavelength range λ2e is observed.

Definitions

For the purposes of the present invention, the term "at least one" means one or more, preferably one, two, three, four, five, six or seven, more preferably one, two, three, four, or five, even more preferably one, two, or three, and most preferably one or two. The same applies to the term "one or more". Further, the terms "two or more" or "at least two" denote that minimum two of the recited components be present, but allows for the presence of further types of the same component, such as three, four, five, six or seven, more preferably two, three, four, or five, even more preferably two or three, and most preferably two.

If, in the present description, an embodiment, feature, aspect or mode of the invention is stated to be preferred, it should be understood that it is preferred to combine the same with other preferred embodiments, features, aspects or modes of the invention, unless there are evident incompatibilities. The resulting combinations of preferred embodiments, features, aspects or modes are part of the disclosure of the present description.

The term "comprising" is used open-endedly. Accordingly, e.g. a composition "comprising" a certain component may contain other components in addition. The term however also includes the meanings of "consisting of" and "consisting essentially of", as far as this is technically possible.

The term "ink" shall denote any material in liquid or viscous form that can be used in a printing, stamping or spraying process. The inks used in the present invention can be suitably selected from screen printing inks, gravure printing inks, inkjet inks, intaglio printing inks, bar coater inks, offset printing inks stamping ink, glue, spraying ink, or varnishes.

"Visible range" means from 400 to 700 nm, "UV range" from 40 to less than 400 nm and "IR range" from more than 700 nm to 2400 nm.

"Fluorescence" denotes the emission of electromagnetic radiation from an excited state of a material having a lifetime τ if less than $10^{-5}$ seconds in terms of exponential decay according to $e^{t/\tau}$, where t denotes time in seconds.

"Phosphorescence" denotes the emission of electromagnetic radiation from an excited state of a material having a lifetime τ of $10^{-5}$ seconds or longer in terms of exponential decay according to $e^{\tau/t}$, where t denotes time in seconds.

In the present invention, all properties relate to those at 20° C. and standard pressure ($10^5$ Pa), unless stated differently.

A partial spatial overlap is characterized by an area in or on a substrate wherein, when seen from an axis extending perpendicular to the plane of the substrate, there are three areas recognizable under certain viewing conditions: An area wherein MAT1, but not MAT2 is provided, an area wherein MAT2, but no MAT1 is provided, and an area wherein both MAT1 and MAT2 are provided. The certain viewing conditions may in some embodiments include only wavelengths of the visible range, but may in other embodiments also include or consist of wavelengths in the UV and/or IR range.

A full spatial overlap is characterized by an area wherein both MAT1 and MAT2 are provided when seen from an axis extending perpendicular to the plane of the substrate. There may be one or more areas wherein additionally only MAT1 or, alternatively, only MAT2 is provided, as long as there are no two or more areas wherein only MAT1 and only MAT2, respectively, are provided. An example of a full overlap in this sense is given in FIG. 1.

BRIEF DESCRIPTION OF THE DRAWINGS

FIGS. 3a, 3b-I and 3b-II show flow diagrams of examples of an authentication procedure according to the invention, where FIGS. 3b-I and 3b-II show a more detailed example including image acquisition and processing.

DETAILED DESCRIPTION OF THE INVENTION

Figure 1:
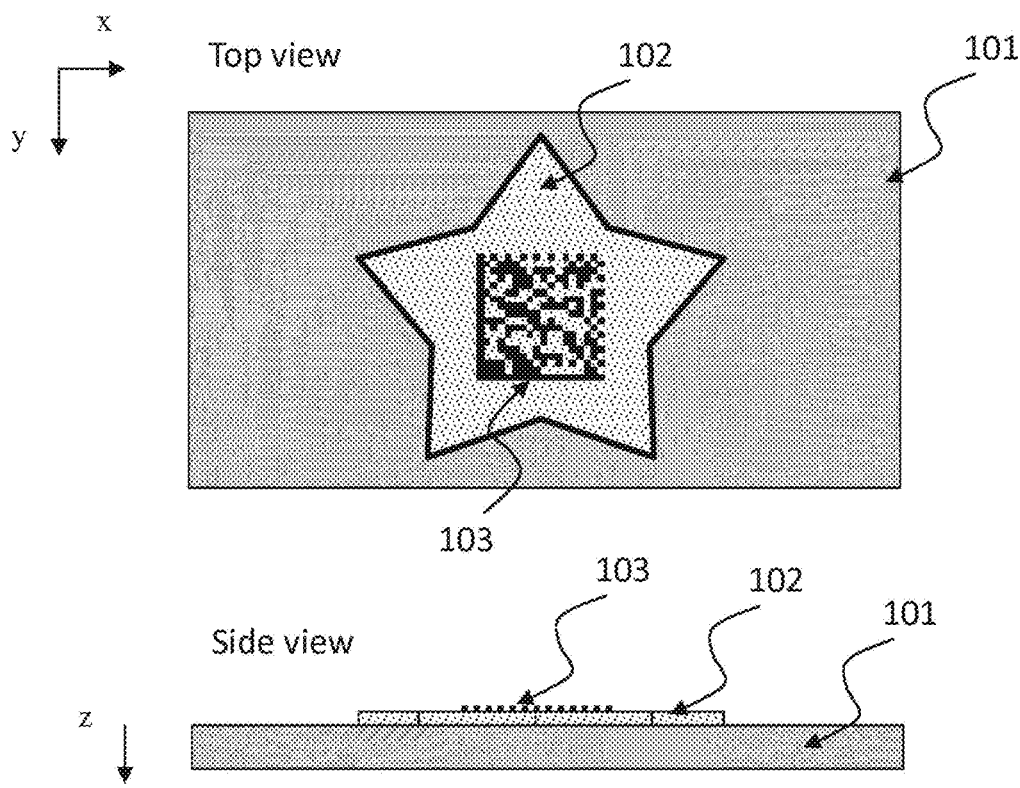
FIG. 1 shows an example of a mark according to the invention comprising a substrate 101 (e.g. a label or product to be marked), onto which a patch or logo 102 is applied with MAT1 (INK1) on top of which a pattern (e.g. a code) 103 is printed with MAT2 (INK2).

The present invention is directed to a security elements thrilled from at least two materials (referred to in the following as MAT1 and MAT2, respectively). MAT1 comprises a phosphorescent pigment (also referred to as "donor" in the following), and the second material MAT2 comprises a fluorescent dye or pigment (also referred to as "acceptor" in the following.) Each of the two materials is arranged within or on one or both surfaces of a substrate made of any suitable material, e.g. paper, cardboard, transparent, translucent or opaque plastics, or other material, such as to partially or fully overlap spatially, as seen by an observer looking at the substrate or an article carrying the security element, from a position along a line extending perpendicular to the plane of the substrate.

Wavelengths and Wavelength Ranges

The phosphorescent pigment (donor) present in MAT1 is capable of emitting phosphorescence radiation in at least one first phosphorescence emission wavelength range $\lambda 1e$ upon excitation by electromagnetic radiation falling within a phosphorescence excitation wavelength range $\lambda 1a$. Further, the fluorescent dye or pigment (acceptor) present in MAT2 is capable of emitting fluorescence radiation in at least one second fluorescence emission wavelength range $\lambda 2e$ upon excitation by electromagnetic radiation falling within a fluorescence excitation wavelength range $\lambda 2a$ of the fluorescent dye or pigment. Herein, the donor and acceptor are selected such that there is a spectral overlap between the phosphorescence emission wavelength range $\lambda 1e$ of the donor and the fluorescence excitation wavelength range $\lambda 2a$. In consequence, the phosphorescence emission emitted by the donor is capable of exciting the fluorescence of the acceptor. This is also referred to as "the luminescence cascade effector simply "cascade effect" in the present invention.

Herein, the term "wavelength range" in the above ranges $\lambda 1a$, $\lambda 1e$, $\lambda 2a$, and $\lambda 2e$ refers to such a set of wavelength values for which the respective spectrum (i.e. excitation or emission) is non-zero, i.e. those wavelength values for which a spectrum response is measurable. For example, in many cases this denotes a range around a peak at a wavelength $\lambda$max in which a spectral response (i.e. excitation in the case of an excitation spectrum or emission in the case of an emission spectrum) is observed. More precisely, it may define the area around a peak value $\lambda$max in a normalized and background-subtracted emission or excitation spectrum, as measured e.g. on a transparent substrate such as a plastic (e.g. polyester) film or carrier, including the respective peak and the shoulders thereof up to the points where the line of the normalized and background-subtracted spectrum crosses the baseline (i.e. the reading in the normalized and background-subtracted spectrum where the observed value becomes zero). This range may be centered at the respective peak $\lambda$max.

In the case that a spectrum is dominated by one peak, a wavelength range may thus be regarded as the breadth of the respective peak in an excitation or emission spectrum. As one example, if a given first dye or pigment exhibits a peak in an excitation spectrum at 450 nm, and breadth of this peak extends to wavelengths of 440 and 460 nm, respectively, the excitation wavelength range is from 440 to 460 nm.

Figure 2:
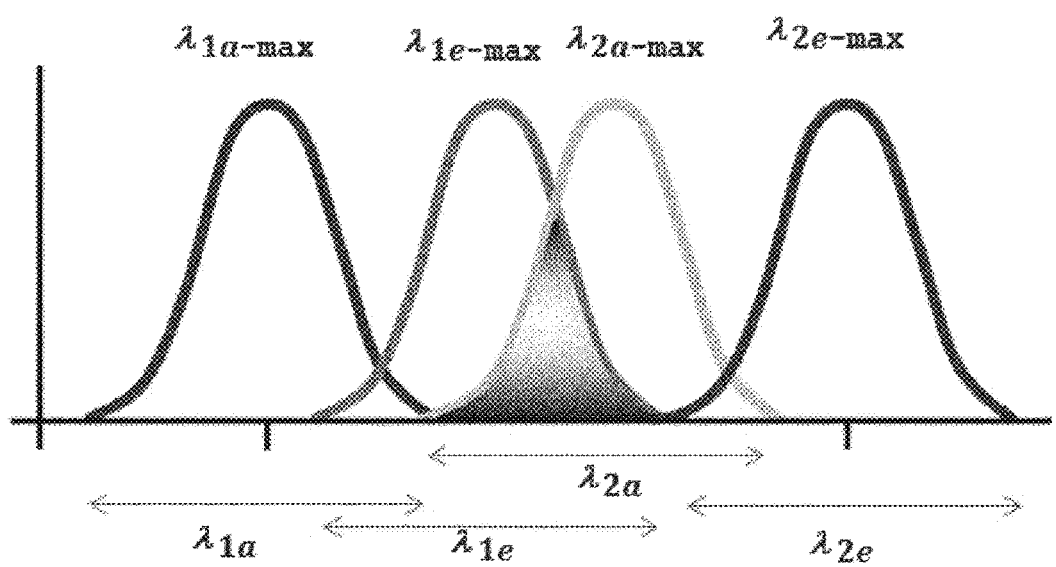
FIGS. 2 and 2a-2e show a schematic representation of an example relationship of the excitation wavelength regions and emission wavelength regions of the phosphorescent pigment (donor) in MAT1 and the fluorescent material (acceptor) in MAT2.

The cascade effect is illustrated in FIG. 2, where $\lambda_{1a}$ is an excitation range of MAT1, $\lambda_{1e}$ is an emission range of MAT1, $\lambda_{2a}$ is an excitation range of MAT2, $\lambda_{2e}$ is an emission range of MAT2, $\lambda_{1a\text{-}max}$ is a peak maximum of excitation of MAT1, $\lambda_{1e\text{-}max}$ is a peak maximum of emission of MAT1, $\lambda_{2a\text{-}max}$ is a peak maximum of excitation of MAT2, and $\lambda_{2e\text{-}max}$ is a peak maximum of emission of MAT2. As shown in FIG. 2, the degree of overlap of the light emitted by the donor within the excitation wavelength range of the acceptor (and the intensity) are chosen to be sufficient to excite the acceptor to emit light. Therefore, the term "the emission of the phosphorescent pigment in MAT1 in the wavelength range $\lambda 1e$ overlaps with at least one excitation wavelength range $\lambda 2a$ of the fluorescent dye in MAT2" denotes that there is an overlap in the respective spectral ranges in the emission wavelength range of the phosphorescent pigment (donor) present in MAT1 and the excitation wavelength range of the fluorescent dye or pigment (acceptor) present in MAT2. Taking the above example of a phosphorescent pigment (donor) having a first excitation wavelength range $\lambda 1e$ of 440 to 460 nm, a spectral overlap is given if an excitation wavelength range of the fluorescent dye or pigment (acceptor) in MAT2, i.e. $\lambda 2a$, includes the values of 440 nm or 460 nm, respectively. As one example, an overlap is given if $\lambda 1e$ of the donor is from 440 to 460 nm, and $\lambda 2a$ of the acceptor is from 450 to 470 nm. A spectral overlap in the sense of the present invention is, however, not given if merely the end values of the ranges are the same, such as in the case of $\lambda 1e$=440 to 460 nm and $\lambda 2a$=460 to 480 nm.

According to the above definition, a small overlap in the respective ranges $\lambda 1e$ and $\lambda 2a$ suffices, as also then a cascade effect in the sense of the present invention occurs. The occurrence of the cascade effect is, however, the more pronounced the more there is a degree of overlap between a phosphorescence emission wavelength range $\lambda 1e$ of the donor and an excitation wavelength range $\lambda 2a$ of the acceptor. In preferred embodiments of the present invention, the "wavelength range" can be taken in a narrower fashion, in order to ensure a stronger degree of overlap between $\lambda 1e$ and $\lambda 2a$. Accordingly, the term "wavelength range" preferably denotes the span of wavelength values, in a normalized and background-subtracted emission or excitation spectrum, up to and including the wavelengths where the line of the normalized and background-subtracted peak falls to a value of n % (0<x≤100) of the peak value at the wavelength λmax, e.g. 10%, more preferably 25%, further more preferably 50% of the peak value at the wavelength λmax, Due to such a narrower "wavelength range", which includes only spectrum values larger than n % (such as 10%, 25% or 50%) of the spectrum amplitude at the maximum, the requirement of an overlap between the (narrower) wavelength ranges leads to a greater overlap between the entire emission spectrum of the donor and the entire excitation spectrum of the acceptor.

Considerations for choice of materials as donor and acceptor to obtain a sufficient "spectral energy transfer" allowing a cascade effect can also be expressed as follows. The spectral energy transfer ratio SE of the cascade effect can be defined as the percentage of area under the normalized (i.e. divided by the maximum spectral amplitude) excitation spectrum of the acceptor A2(λ) that also falls under the normalized emission spectrum of the donor E1(λ).

Figure 2A:
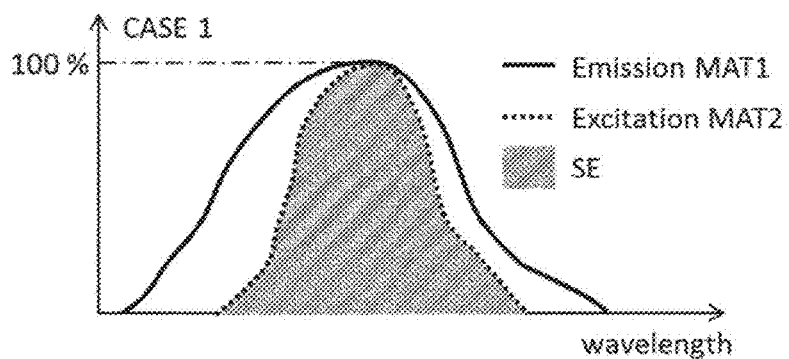

According to a preferred example, the excitation spectral range of the acceptor fully falls within the emission spectral range of the donor (CASE1, see FIG. 2a). In other words, 100% of the excitation spectrum of the acceptor is included/comprised inside the emission spectrum of the donor, and the above defined spectral energy transfer ratio is 100%.

Even more preferably, compared to the situation represented in FIG. 2a, the emission spectrum of the donor could exactly match the excitation spectrum of the acceptor so that the whole emission energy of the donor can potentially be transferred to the acceptor. However this situation can rarely be achieved because only a few combinations of materials (pigments and dyes) can satisfy it.

However, other choices of materials are also possible. For example CASE 2 in FIG. 2b where a fraction of, but not the entire, excitation spectrum of the acceptor falls within the emission spectrum of the donor. In this example, the dashed area under A2(λ) that also falls under E1(λ) represents 50% of the total area under A2(λ), such that SE is 50%, Preferably, SE should be larger than 50%, and more preferably larger than 70%.

Figure 2B:
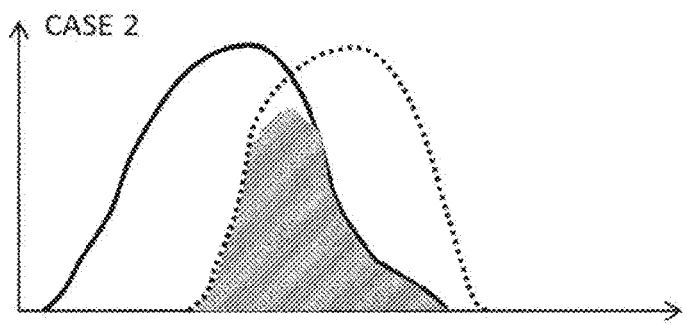

In CASE 2 according to FIG. 2b, a fraction of the acceptors cannot be excited by the donor because no or little photons are emitted by the donor in a part of the excitation wavelength range of the acceptor. In addition, a fraction of the emission of the donor cannot be used to excite the acceptor because it falls within wavelengths that are outside of the excitation spectrum of the acceptor.

Figure 2C:
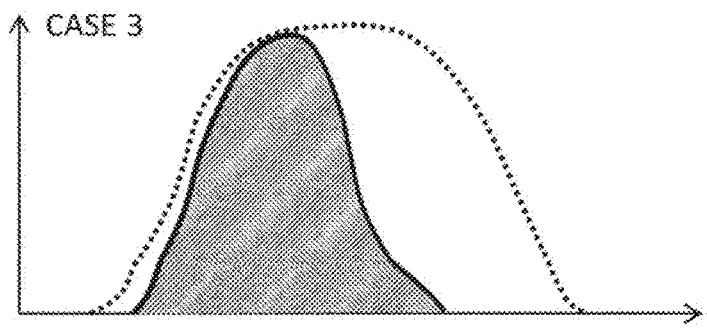

An alternative case (CASE 3 in FIG. 2c) can be envisioned where also 50% of the area under A2(λ) is overlapped by the emission spectrum E1(λ) of the donor, but the whole emission spectrum E1(λ) is enclosed within A2(λ). In this case, all the emitted energy by the donor can potentially be transferred to the acceptor.

Figure 2D:
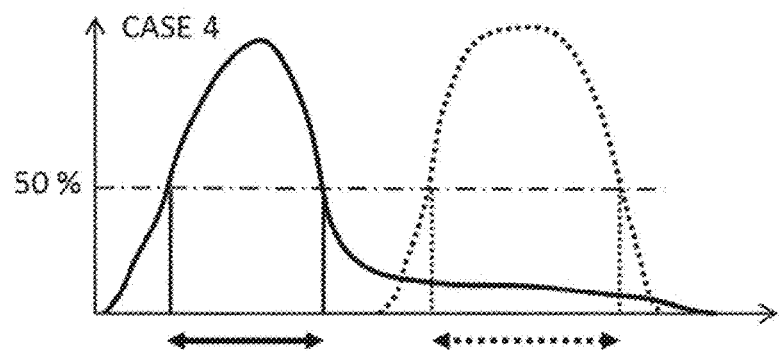

There are, however, other cases possible, such as CASE 4 illustrated as an example in FIG. 2d. Here, although the excitation spectral range of the acceptor is completely overlapped by the donor emission spectrum, the spectral energy transfer ratio would be rather low because the emission spectrum intensity is very low in the region of overlap.

As a consequence, and as described above, the requirement of overlapping spectral ranges can be chosen such that both spectral ranges may only include spectrum values larger than n % of the spectrum amplitude at the maximum (e.g. 50% in FIG. 2d). Then a condition for the spectral energy transfer ratio to be sufficient could be expressed in terms of the ratio of wavelength range where an overlap occurs, to the excitation spectral range (as defined above) of the acceptor. Preferably this ratio is 50% or more, more preferably 70% or more and most preferably, 100%.

Figure 2E:
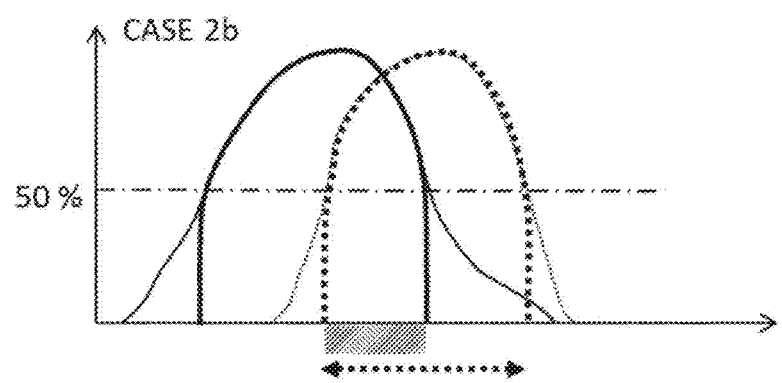

FIG. 2e shows CASE 2b which is an alternative representation of CASE 2 of FIG. 2b (same spectra), but using the criterion defined in terms of wavelength ranges for intensity exceeding 50% of maximum. In this example, the ratio of spectral range overlap to the excitation spectral range of the acceptor is about 50%, which is the same as the criterion using the area of FIG. 2b.

Figure 5:
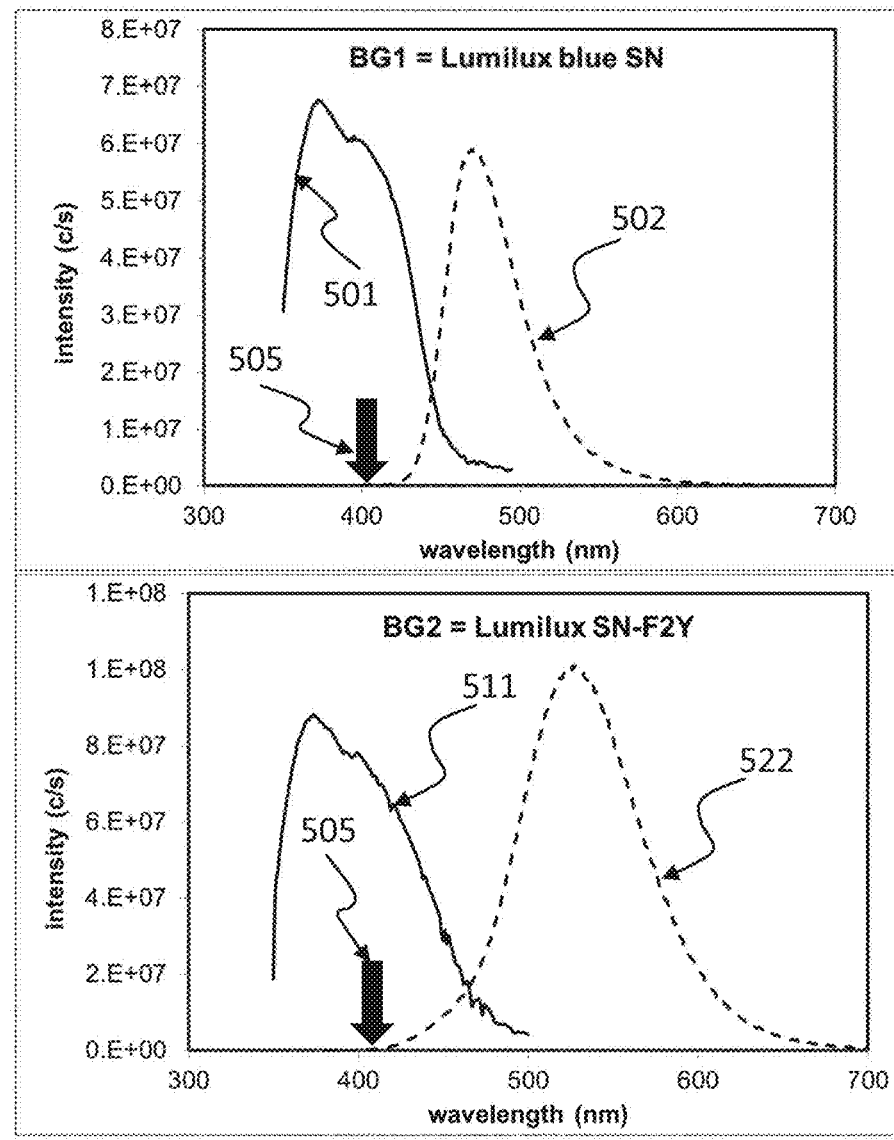
FIG. 5 shows excitation and emission spectra of 2 different possible long afterglow phosphors (BG1 and BG2).
Figure 6:
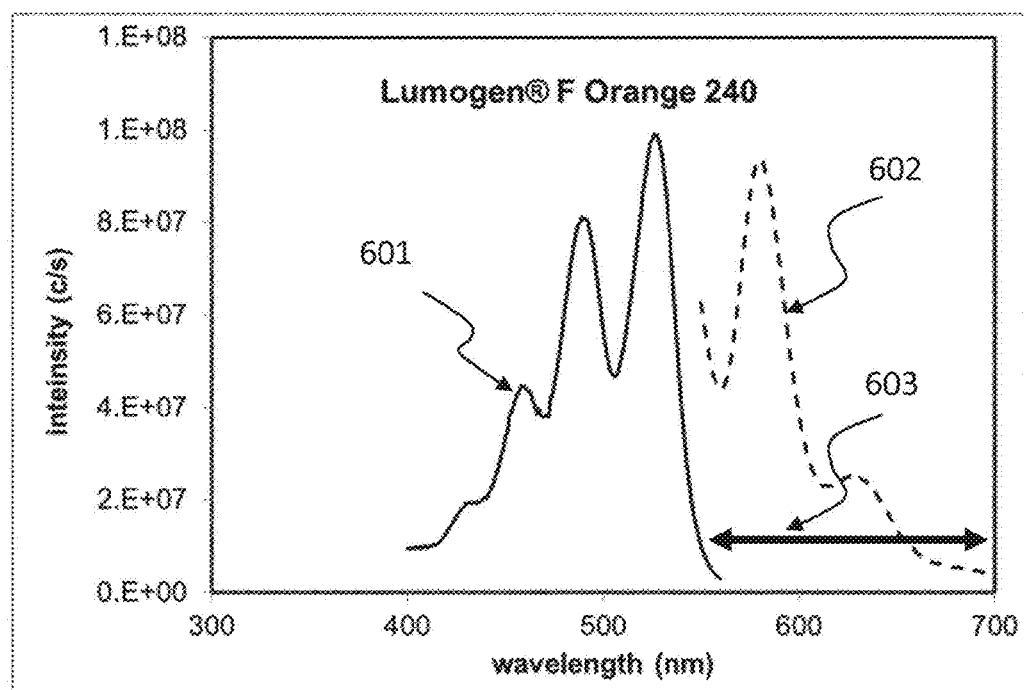
FIG. 6 shows excitation and emission spectra of the fluorescent dye in MAT2 (INK2) used for the detailed example of the invention, along with the measurement spectral range.

In the context of the examples described further on in the application using as donor the Lumilux phosphors, which spectra are shown in FIG. 5 and as acceptor the Lumogen Orange (spectra in FIG. 6), it can be said that both combinations (using either BG1 or BG2 Lumilux) represents CASE1, which is the most favorable. FIGS. 5 and 6 show that the entire excitation spectral range of the acceptor (Lumogen, 420-550 nm) is fully enclosed within the emission spectral range of either BG1 (420-570 nm) or BG2 (420-640 nm).

In another preferred embodiment, the respective ranges λ1e and λ2a overlap in such a manner that the overlap in the ranges (calculated from the peak wavelengths up to the wavelengths where the line crosses the baseline, i.e. the value in the respective spectrum becomes zero) is such that 20% or more, more preferably 50% or more, and particularly preferably 70% or more of the wavelengths included in the range λ1e are encompassed by the range λ2a.

In the present invention, it assumed that the donor emits phosphorescence light, which then, due to the overlap between λ1e and λ2a, excites the acceptor to emit light in a another wavelength region. However, without wishing to be bound by theory, the energy transfer from the first dye to the second dye may also be a radiationless transfer (so-called Foerster resonance energy transfer, FRET). Since it is a requirement for both a radiationless Foerster-type energy transfer and an energy transfer by radiation that there is an overlap between the emission spectrum of the donor and the excitation spectrum of the acceptor, it is without relevance for the present invention whether the energy transfer between the donor and the acceptor is radiationless or includes emission of radiation from the donor and absorption of the radiation (for excitation) by the acceptor, or is produced by the combination of radiationless and radiation transfer, see also D. L. Andrews, A UNIFIED THEORY OF RADIATIVE AND RADIATIONLESS MOLECULAR ENERGY TRANSFER; Chemical Physics 135 (1989) 195-201.

It is preferred that the donor displays an excitation peak in its excitation spectrum at a wavelength (λ1a-max) that is shorter than the wavelength (λ2a-max) at which the acceptor displays an excitation peak in its excitation spectrum, i.e. that λ1a-max (nm)<λ2a-max (nm).

It is also preferred, in this and other embodiments of the invention, that the donor displays a maximum emission in its emission spectrum at a wavelength (λ1e-max) that is shorter than the wavelength (λ2e-max) at which the acceptor displays a maximum emission in its excitation spectrum, i.e. that λ1e-max (nm)<λ2e-max (nm).

It is further preferred that λ1a-max<λ1e-max<λ2a-max<λ2e-max, as illustrated in FIG. 2. This is however not mandatory, as an overlap between λ1e and λ2a can also be realized if λ1e-max>λ2a-max. Accordingly, in one embodiment of the present invention λ1a-max<λ2a-max<λ1e-max<λ2e-max.

Typically, the emission peak wavelength of any dye or pigment is located at longer wavelengths than the respective excitation peak wavelength, i.e. $\lambda$2a-max<$\lambda$2e-max and $\lambda$1a-max<$\lambda$1e-max. In this case, the emission occurs at longer wavelengths (at lower energy) as compared to the respective excitation. It is however also possible to use, as donor, a so-called anti-Stokes material, where the emission occurs at shorter wavelengths as compared to the respective excitation, i.e. $\lambda$1a-max>$\lambda$1e-max. In such an embodiment, $\lambda$2a-max may be at shorter or longer wavelengths as compared to $\lambda$1e-max.

The distance between the two excitation peaks of the donor and acceptor, i.e. ($\lambda$2a-max)−($\lambda$1a-max), is for instance at least 5 nm, e.g. 5 to 500 nm, 10 to 200 nm, 20 to 80 nm, 30 to 70 nm, and preferably 50 to 200 nm. A distance of at least 20 nm is preferred in order to avoid excitation of the acceptor by the irradiation of the electromagnetic radiation that is intended to excite the donor dye or pigment in an authentication method. However, this requirement does not need to be satisfied in case that the time-dependent decay feature of the security element of the present invention is utilized for authentication purposes.

The absolute distance between the emission peak $\lambda$1e-max of the donor and the excitation peak of the acceptor $\lambda$2a-max, i.e. ABS(($\lambda$2a-max)−($\lambda$1e-max)) is for instance at most 20 nm. A smaller difference is preferable, since then a greater overlap between $\lambda$2a and $\lambda$1e can be ensured.

The wavelength at which a dye or pigment displays a peak in the excitation spectrum ($\lambda$a-max) or emission spectrum ($\lambda$e-max), and the respective excitation and emission wavelength ranges are measured as follows.

Notably, in the present invention all measurements are performed at room temperature (20° C.), and consequently the peak wavelengths $\lambda$1a-max, $\lambda$1e-max, $\lambda$2a-max, and $\lambda$2e-max as well as the respective ranges $\lambda$1a, $\lambda$1e, $\lambda$2a, and $\lambda$2e are those measured at room temperature according to the following procedure:

First of all, a blank of MAT1 is prepared, which is ensured to be formulated such as not to interfere with the phosphorescence of the donor, both chemically and optically. A composition that was found to serve this purpose well is composed of 31.5 wt.-% Tripropyleneglycol diacrylate monomer, 17.9 wt.-% trimethylolpropane triacrylate, 19.0 wt.-% EBECRYL™ 2959, 11.6 wt.-% EBECRYL™ 80, 2.1 wt.-% TEGO® Airex 900, 1.0 wt.-% GENORAD™ 20, 9.5 wt.-% Calcium carbonate, 2.1 wt.-% Benzyl dimethyl ketal and 5.3 wt.-% IRGACURE® 1173. While this system is preferably used for the present invention, also other systems can be employed as long as it is ensured that there is no or very little interference with the fluorescence of the donor and acceptor dyes, both chemically and optically.

Then, a blank of MAT2 is prepared, which is ensured to be formulated such as not to interfere with the fluorescence and phosphorescence of the donor and acceptor, both chemically and optically. A composition that was found to serve this purpose well is composed of 87 wt.-% Methylethylketone, 10.3 wt.-% of a hydroxyl-containing copolymer made from 84 wt.-% vinyl chloride and 16 wt.-% of acrylic acid ester (commercially available from Wacker Chemie under the tradename VINNOL E15/40 A) and 2% of a terpolymer made from 84 wt.-% vinyl chloride, 15 Gewwt.-% vinyl acetate and 1 wt.-% dicarboxylic acid (commercially available from Wacker Chemie under the tradename VINNOL E15/45 M). While this system is preferably used for the present invention, also other systems can be employed as long as it is ensured that there is no or very little interference with the fluorescence of the donor and acceptor dyes, both chemically and optically.

Then MAT1 composition is prepared by dispersing 15% of the donor in the above MAT1 blank. This is used for determining the wavelength peak and the wavelength ranges for both emission and excitation for the pigment in the MAT1 ink.

Then MAT2 composition is prepared by dispersing 1.23% of the acceptor in the above MAT2 blank. This is used for determining the wavelength peak and the wavelength ranges for both emission and excitation for the fluorescent dye in the MAT2 ink.

For the two compositions, samples having 12 µm wet film deposit thickness are then prepared, using e.g. a K Control Coater from RK Print Coat Instruments, e.g. the HC2 coating bar, on a suitable white substrate (e.g. the white part of LENETA N2C-2 substrates), followed by UV curing and drying at room temperature for MAT1 and MAT2, respectively. Then, the drawdown samples are measured in emission and excitation mode using a commercial Horiba Fluorolog III (FL-22) as further described below.

Horiba Fluorolog III Measurement Conditions:

The instrument used to perform emission and excitation spectra measurement is a commercial twice double monochromator equipped with a continuous Xe arc lamp as illumination source and a Hamamatsu R928P photomultiplier tube operated in photon counting mode as detector. The flat sample is positioned so that its normal direction is at an angle of 30 degrees with respect to the irradiation optical axis. The Fluorolog-III type of light collection method used is "Front Face". In this collection mode, the emission collection is performed at an angle of 22.5 degrees with respect to the irradiation beam. By using this collection method and setup, it is ensured that collecting direct specular reflection from the sample is avoided. Both excitation and emission monochromators are double monochromators fitted with 1200 grid/mm holographic gratings blazed at 500 nm.

For excitation spectrum measurement, as shown for instance in the curves 501 and 505 on the left of both plots of FIG. 5, the following procedure is adopted: the emission monochromator is set at a given wavelength (the one where the emission is to be measured, for example 530 nm in the lower spectrum of FIG. 5) and the excitation monochromator is scanned at 1 nm increment, over the wavelength range where the excitation spectrum is to be measured (e.g. 350 to 500 nm). At each excitation wavelength increment, a measurement of the emission signal is recorded by the detector using a 100 ms integration time. As known to the skilled person, since the irradiation source is not spectrally flat, a suitable irradiation correction is applied onto the measured signal at every wavelength using an appropriate spectral calibration. A spectral correction of the detector sensitivity is also applied. The spectrally corrected excitation spectrum can hence be reconstructed.

For emission spectrum measurement, the excitation monochromator is set to the desired excitation wavelength (e.g. at 380 nm for the upper plot of FIG. 5) and the emission monochromator is scanned over the desired emission spectral range (400 to 600 nm for upper plot of FIG. 5 for example) at 1 nm increment while recording the detector signal at each wavelength with a 100 ms integration time. The emission spectrum is then constructed from all recorded data points and after having applied the suitable spectral sensitivity corrections of the instrument.

The spectral calibration of the Fluorolog III excitation channel is made using a procedure that is commonly applied by persons skilled in the art: the spectral irradiance is measured using a calibrated detector (e.g. a reference photodiode) positioned at the location of the sample. This is made for all wavelengths by scanning the excitation monochromators. This reference detector has a known spectral response (sensitivity as a function of the wavelength of radiation impinging on it) that has been previously determined by measuring an irradiation standard (e.g. a calibrated tungsten ribbon lamp) in a laboratory. An excitation spectral calibration curve is then calculated by dividing the real spectral sensitivity of the used reference detector by the measured spectral irradiance. This calibration curve can then be used to correct the spectral response to excitation of any further measurement by simple multiplication.

A spectral sensitivity calibration of the emission measurement channel of the Fluorolog III is performed in an analogue way by using a spectral irradiance standard (e.g. a tungsten ribbon lamp, which spectral irradiance has been determined in a laboratory), This lamp is disposed at the location of the sample and spectral emission is recorded by the Fluorolog III detector during scanning the emission monochromators. An emission spectral sensitivity curve is obtained by dividing the spectral irradiance curve of the standard irradiance source by the measured spectral curve. Further measurements are then corrected by multiplication by the spectral emission calibration curve.

These calibration procedures are repeated regularly to ensure correction of any instrument drift or detector/Xe lamp ageing.

The overall spectral resolution of the instrument for both emission and excitation measurements is 0.54 nm FWHM (Full Width at Half Maximum), for the slits configuration used in the measurement conditions described above.

The same above procedure is followed for all different sample measurements; only the spectral ranges for the excitation and emission spectrum measurements, along with the excitation and emission fixed wavelengths may differ depending on the dye in the samples.

As derivable from the above, since the measurements shall serve to evaluate the spectral properties in the final composition, the donor is dispersed in a blank composition at a concentration of 15 wt.-% and the acceptor dye is dissolved in a blank composition at a concentration of 1.23 wt.-%. Then, emission and excitation spectra are recorded, separately for each dye/pigment and composition, and under the same conditions as for the blank. For each dye and ink, the background is subtracted and the spectrum normalized (with the highest peak having an intensity of 1.0), and the peak wavelength(s) $\lambda_{max}$ and the emission and excitation wavelength ranges $\lambda 1a$, $\lambda 1e$, $\lambda 2a$ and $\lambda 2e$ are determined by determining the points where the spectrum returns to baseline (or to 10, 25 or 50% above baseline, depending on the definition of the term "wavelength range" as discussed above).

These measurements thus provide the wavelength ranges $\lambda 1a$, $\lambda 1e$, $\lambda 2a$ and $\lambda 2e$ and the respective wavelengths of the peaks $\lambda 1a$-max, $\lambda 1e$-max, $\lambda 2a$-max and $\lambda 2e$-max. These values are then used to determine whether or not the cascade effect requirements of the present invention are satisfied, i.e. whether the requirement of an overlap between the ranges $\lambda 1e$ and $\lambda 2a$ is satisfied. These measurements can also be used to identify suitable dyes and pigments as acceptor and donor for the purposes of the present invention.

In the above explanations, it was assumed that each fluorescent dye or pigment exhibits only one excitation peak ($\lambda 1a$-max, $\lambda 2a$-max) and one emission peak ($\lambda 1e$-max, $\lambda 2e$-max), and only one corresponding excitation wavelength range ($\lambda 1a$, $\lambda 2a$) and one emission wavelength range ($\lambda 1e$, $\lambda 2e$). While this is true for many dyes and pigments, a considerable number of dyes and pigment show multiple excitation peaks and multiple emission peaks (see FIG. 6). In such cases, each peak in the normalized spectrum reaching an intensity of 0.5 or more (preferably 0.75 or more) may serve as emission peak ($\lambda 1e$, $\lambda 1e$) or absorption peak ($\lambda 1a$, $\lambda 2a$) for the purposes of the present invention, so that there may be multiple $\lambda 1e$ and $\lambda 1a$, or multiple $\lambda 2e$ and $\lambda 2a$.

The explanations above then apply to each of the peaks and Wavelength ranges. For instance, it is sufficient that there is an overlap between any $\lambda 1e$ and any $\lambda 2a$, so that energy can be transferred from the donor to the acceptor.

When an excitation or emission spectrum of a dye or pigment used in the present invention shows several overlapping peaks, the peaks and wavelength ranges are obtained by fitting the obtained spectrum using a suitable software (least square method), such as for instance OCTAVE. Herein, a spectrum of overlapping peaks can be satisfactorily (Goodness of Fit<0.1) simulated by assuming an overlap of two (or rarely three) peaks, and the simulated values are taken for the identification of the peak wavelengths and for the identification of the wavelength ranges.

Dyes and Pigments

Generally speaking, both the acceptor and donor preferably show excitation bands and emission bands in the range of 40 to 2400 nm, in particular 300 to 1100 nm. Preferably, the donor shows emission hands, in particular the maximum emission, in the UV range or visible range (in particular 300 to 700 nm), and the acceptor excitation bands (to be excited by the donor), in particular the maximum excitation, in the visible or IR range (in particular 400 to 1100 nm). "Visible range" means from 400 to 700 nm, "UV range" from 40 to less than 400 nm and "IR range" from more than 700 nm to 2400 nm. More specifically, the donor dye preferably shows emission band(s) matching acceptor dye excitation band(s) in the range 250-900 nm Fluorescent dyes and pigments and phosphorescent pigments adequate for preparing the materials MAT1 and MAT2 of the invention and for implementing the authentication method can be suitably selected from commercially available dyes and pigments. They can for instance be selected from the following substance classes:

Cyanines (polymethines) and the related cyanine-type chromophors, quinones and the related quinone-type chromophors, porphines, phtalocyanines and the related macrocyclic chromophors as well as polycyclic aromatic chromophors.

Cyanine (polymethine) dyes are known in the art and used as photographic sensitizers (D. M. Sturmer, The Chemistry of Heterocyclic Compounds, Vol 30, John Wiley, New York, 1977, pp 441-587; Eastman Kodak). In a more recent application, stable representatives of this compound class, selected from the coumarins and rhodamines, were also used as laser dyes (J. B. Marling, J. H. Hawley, E. M. Liston. W. B. Grant, Applied Optics, 13(10), 2317 (1974)). Known fluorescent Rhodamine dyes include e.g. Rhodamine 123, Rhodamine 6G, Sulforhodamine 101, or Sulforhodamine B.

Phthalocyanines and related dyes are the "industrial variant" of porphines and include a greater number of well-known fluorescent dyes. They generally absorb at the long wavelength end of the visible spectrum. The class of phtalocyanines at large comprises as well the higher-conjugated analogs, such as the naphthalocyanines, which absorb farther in the IR, as well as the heterosubstituted analogs of phtalocyanines; the common point defining this compound class is that all of its members are derived from aromatic ortho-dicarboxylic acids or from their derivatives.

Quinone dyes are known in the art and used for textile and related dying applications (e.g. indigoid dyes, anthraquinone dyes, etc.). Electronegative groups or atoms along the quinone skeleton can be present to enhance the intensity of the absorption band, or to shift it to longer wavelengths.

Fluorescent aromatic polycyclic dyes include a rigid, planar molecular structure (similar to the graphite lattice) which may carry substituents. Typically the planar molecular structure comprises at least two fused aromatic benzene rings (e.g. 2 to 6 rings), in one of the fused aromatic rings, e.g. the central ring of three fused six-membered aromatic rings, one or two carbon atoms may be replaced by C=O, O and/or N. Fluorescent members of this class of dyes and pigments can be selected e.g. from perylenes (e.g. Lumogen F Yellow 083, Lumogen F Orange 240, Lumogen F Red 300, all available from BASF AG, Germany), naphtalimides (e.g. Lumogen F Violet 570, available from BASF AG, Germany) quinacridones, acridines (e.g. Acridine orange, Acridine yellow), oxazines, dioxazines, or fluorones (e.g. Indian Yellow) are examples of such dyes.

Fluorene copolymers, also called luminescent conjugated polymers can be used as dyes in the MAT2. Examples are referenced in US2003/0154647 A1 (U.S. Pat. No. 6,808, 542).

Similarly to the dye, the pigment is not particularly limited as long as it has the required spectral properties and is capable of showing fluorescent or phosphorescent emission in a suitable wavelength region. Useful pigments include virtually all fluorescent and phosphorescent pigments known to the skilled person. Such pigments are well-known to the skilled person, and many such pigments are commercially available. They can generally be identified in the following classes of compounds 1) Semiconductors of III-type, such as GaAs, GaP, GaAsP, GaSb, InAs, InP, InSb, AlAs, AlP and AlSb or II-VI type, such as CdS, CdSe, CdTe, HgS, ZnS, which are doped with a species selected from groups 1 (Li, Na, K, Rb, Cs), 2 (Be, Mg, Ca, Sr), Al, Cr, Tl, Mn, Ag, Cu, As, Nb, Ni, Ti, In, Sb, Ga, Si, Pb, Bi, Zn, Co and/or group 3 (e.g. Sc, Y, La), or lanthanides (elements 58 to 71, i.e. Ce, Pr, Nd, Pm, Sm, Eu, Gd, Tb, Dy, Ho, Er, Tm, Yb and Lu).

2) Fluorescent, doped metal oxides, such as those described in U.S. Pat. No. 6,309,701, including host metal oxide such as $Y_2O_3$, $ZrO_2$, ZnO, CuO, $CuO_2$, $Gd_2O_3$, $Pr_2O_3$, $La_2O_3$, and mixed oxides, being doped with at least one rare earth metal (hereinafter to be understood as Sc, Y, La and the elements 58 to 71), in particular Eu, Cc, Nd, Sm, Tb, Gd, Ho, and/or Tm;

3) Optionally doped metal salts of wherein the anion is preferably selected from phosphates, halophosphates, arsenates, sulphates, borates, aluminates, gallates, silicates, germanates, vanadates, niobates, tantalates, wolframates, molybdates, alkalihalogenates, other halides (in particular fluorides and iodides), nitrides, sulphides, seicnides, sulphoselenides, as well as oxysulphides. The metals preferably belong to the main groups 1, 2, 13, or 14, the subgroups 3, 4, 5, 6, 7, or the lanthanides. The dopant metal is preferably selected from groups 1 (Li, Na, K, Rb, Cs), 2 (Be, Mg, Ca, Sr), Al, Cr, Tl, Mn, Ag, Cu, As, Nb, Ni, Ti, In, Sb, Ga, Si, Pb, Bi, Zn, Co and/or group 3 (e.g. Sc, Y, La), or lanthanides (elements 58 to 71, i.e. Ce, Pr, Nd, Pm, Sm, Eu, Gd, Tb, Dy, Ho, Er, Tm, Yb and Lu). One example is for instance CsI with a fluorescent emission around 315 nm. The optional dopant is preferably Eu, Ce, Nd, Sm, Tb, Gd, Ho, Tm, a combination of Ce and Tb or Ce and Dy.

In the following, some examples for luminescent pigments are given which can be used in the present invention: $Bi_4Ge_3O_{12}$ LiI:Eu; NaI:Tl; CsI:Tl; CsI:Na; LiF:Mg; LiF:Mg; LiF:Mg,Ti, LiF:Mg,Na; $KMgF_3$:Mn; $Al_2O_3$:Eu; BaFCl:Eu; BaFCl:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_{14}O_{23}$:Eu; $BaMgAl_{10}O_{17}$:Eu; (Ba, $Mg)Al_2O_4$:Eu; $Ba_2P_2O_7$:Ti; (Ba, Zn, $Mg)_3Si_2O_7$:Pb; Ce(Mg, $Ba)Al_{11}O_{19}$; $Ce_{0.65}Tb_{0.35}MgAl_{11}O_{19}$; $MgAl_{11}O_{19}$:Ce,Tb; $MgF_2$:Mn; MgS:Eu; MgS:Ce; MgS:Sm; MgS(Sm, Ce); (Mg, Ca)S:Eu; $MgSiO_3$:Mn; $_{3.5}MgO_{0.5}MgF_2GeO_2$:Mn; $MgWO_4$:Sm; $MgWO_4$:Pb; $6MgO.As_2O_5$:Mn; (Zn, $Mg)F_2$:Mn; (Zn, $Be)SO_4$:Mn; $Zn_2SiO_4$:Mn; $Zn_2SiO_4$:Mn,As; ZnO:Zn; ZnO:Zn,Si,Ga; $Zn_3(PO_4)_2$:Mn; ZnS:A (A=Ag, Al, Cu); (Zn, Cd)S:A (A=Cu, Al, Ag, Ni); $CdBO_4$:Mn; $CaF_2$:Dy; CaS:A (A=lanthanides, Bi); (Ca, Sr)S:Bi; $CaWO_4$:Pb; $CaWO_4$Sm; $CaSO_4$:A (A=Mn, lanthanides); $3Ca_3(PO_4)_2.Ca(F, Cl)_2$:Sb, Mn; $CaSiO_3$:Mn, Pb; $Ca_2Al_2Si_2O_7$:Ce; (Ca, $Mg)SiO_3$:Ce; (Ca, $Mg)SiO_3$:Ti; $2SrO_6(B_2O_3).SrF_2$:Eu; $3Sr_3(PO_4)_2.CaCl_2$:Eu; $A_3(PO_4)_2.ACl_2$:Eu (A=Sr, Ca, Ba); $(Sr,Mg)_2P_2O_7$:Eu; (Sr, $Mg)_3(PO_4)_2$:Sn; SrS:Ce; SrS:Sm,Ce; SrS:Sm; SrS:Eu; SrS:Eu,Sm; SrS:Cu,Ag; $Sr_2P_2O_7$:Sn; $Sr_2P_2O_7$:Eu; $Sr_4Al_{14}O_{25}$:Eu; $SrGa_2S_4$:A (A=lanthanides, Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides); $Y_3Al_5O_{12}$:Ln (Ln=lanthanides); $YAl_3(BO_4)_3$:Nd,Yb; $(Y,Ga)BO_3$:Eu; $(Y,Gd)BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Ln=lanthanides); $YVO_4$:A (A=lanthanides, In); $Y(P,V)O_4$:Eu; $YTaO_4$:Nb; $YAO_3$:A (A=Pr, Tm, Er, Cc); YOCl:Yb,Er; $LnPO_4$:Ce,Tb (Ln=lanthanides or mixtures of lanthanides); $LuVO_4$:Eu; $GdVO_4$:Eu; $Gd_2O_2S$:Tb; $GdMgB_5O_{10}$:Ce,Tb; LaOBrTb; $La_2O_2S$:Tb; $LaF_3$:Nd,Ce; $BaYb_2F_8$:Eu; $NaYF_4$:Yb,Er; $NaGdF_4$:Yb,Er; $NaLaF_4$:Yb,Er; $LaF_3$:Yb,Er,Tm; $BaYF_5$:Yb,Er; $Ga_2O_3$:Dy; GaN:A (A=Pr, Eu, Er, Tin); $Bi_4Ge_3O_{12}$; $LiNbO_3$:Nd,Yb; $LiNbO_3$:Er; $LiCaAlF_5$:Ce; $LiSrAlF_6$:Ce; $LiLuF_4$:A (A=Pr, Trn, Er, Ce); $Gd_3Ga_5O_2$:Tb; $Gd_3Ga_5O_{12}$:Eu; $Li_2B_4O_7Mn,SiOx$:Er,Al (0<x<2).

In the following detailed description of embodiments and examples, two particular commercial long afterglow phosphor pigments were tested and incorporated at various concentrations: Lumilux® blue SN and Lumilux® green SN-F2Y (Honeywell). The excitation and emission spectra of these pigments are represented in FIG. 5, which shows excitation spectra 501 and 511 and emission spectra 502 and 522 of two phosphorescent pigments used in INK1 for printing a background patch or logo 102 in a detailed example of the invention. Black arrows 505 indicate the wavelength peak of a deep blue LED at 410 nm used for exciting the background. These spectroscopic properties were measured on samples printed with silkscreen ink using a spectrofluorometer (Horiba Jobin Yvon Fluorolog III), wherein the following silk screen blank MAT1 composition was used: 31.5 wt.-% Tripropyleneglycol diacrylate monomer, 17.9 wt.-% trimethylolpropane triacrylate, 19.0 wt.-% EBECRYL™ 2959, 11.6 wt.-% EBECRYL™ 80, 2.1 wt.-% TEGO® Airex 900, 1.0 wt.-% GENORAD™ 20, 9.5 wt.-% Calcium carbonate, 2.1 wt.-% Benzil dimethyl ketal and 5.3 wt.-% IRGACURE™ 1173. Various concentrations of Lumilux® blue SN and Lumilux® green SN-F2Y (Honeywell) in the blank MAT1 were tested ranging from 1% to 30%

The present invention is not restricted to the commercially available pigments. Several host crystals doped with activators and having long persistent phosphorescence can preferably be used, that are more preferably selected from the group consisting of doped host crystals selected from silicates (Ca2Al2SiO7, CaAl2Si2O8, Zn2SiO4,etc.), other oxides, in particular aluminates, lutetium oxides, strontium oxide and germanates (CaAl4O7, CaAl2O4, SrAl2O4, BaAl2O4, Lu2O3, SrO, Zn2GeO4,etc), and non-oxides, such as sulfides (e.g. ZnS). The activators present in these host crystals are preferably selected from rare earths ions or transition metal ions, and more preferably $Ce^{3+}$, $Eu^{2+}$, and $Mn^{2+}$. To obtain a long persistent phosphorescence, a codopant is often suitable in addition to the activator, like for example in $SrAl_2O_4:Eu^{2+}, Dy^{3+}$, whereas the host $SrAl_2O_4$ is codoped with Eu2+ and Dy3+.

Further examples of pigments having a long afterglow can be found in the following references: *Persistent Luminescence in Non-Eu2+-Doped Compounds*, A Review, Materials 2013, 6, 2789-2818 and *Persistent Luminescence in Eu2+-Doped Compounds*, A Review, Materials, 2010, 3, 2536-2566, both incorporated herein by reference.

A suitable donor-acceptor pair can be properly selected from these and other known fluorescent dyes and pigments and phosphorescent pigments based on their spectral properties, which, as a rule, are published by the manufacturer and can be easily measured, as explained above. It however needs to be considered that the excitation behavior of the final material MAT1 and MAT2 as present in the final security element is decisive for obtaining the effect of the invention, so that published data generally should be verified by measuring the absorption and emission spectrum in accordance with the method described above for a printed ink on the final substrate. This is due to the fact that published data may relate to solutions of the dyes in a particular solvent (e.g. $CH_2Cl_2$) wherein the spectral properties may be different from the printed ink, e.g. due to interactions with the substrate. Although generally to a lesser extent, the spectral properties of pigments may also be influenced by the surroundings, so that the same applies.

Even if only the excitation and emission maxima are available (before complete absorption and emission spectra have been measured) an evaluation will be possible to what extent the emission spectrum of the donor is likely to overlap with the excitation spectrum of the acceptor thereby allowing a screening of suitable candidates.

The suitable particle size of the fluorescent dye or pigment for MAT2 is not particular limited. In case it is applied by inkjet, the particle size (as expressed by the average particle diameter measured by a laser scattering technique) is in the range of 300 nm or smaller. If the fluorescent dye of MAT2 is an organic molecules such as Rhodamine or Quinone, or any organic dye as described above, then the dyes are dispersed or solubilized at the molecular level, thus the size of the particle corresponds to the size of the non-aggregated molecule. However, if the particle is an inorganic pigment, then the particles size will be preferably smaller than 300 nm, more preferably smaller than 200 nm, even more preferably smaller than 100 nm. The particle size of the phosphorescent pigment in MAT1 is typically 1 micron or more, preferably 10 microns or more.

MAT1 and MAT2

As outlined above, MAT1 comprises at least one phosphorescent pigment, and MAT2 comprises at least one fluorescent dye or pigment. These have the respective wavelength regions $\lambda 1a$, $\lambda 1e$, $\lambda 2a$ and $\lambda 2e$, so that emission from the phosphorescent pigment can excite the fluorescent dye or pigment to emit fluorescence. Besides these essential pigments and dyes, respectively, further phosphorescent, fluorescent or non-luminescent dyes and pigments may be included in MAT1 and MAT2, as far as thereby the energy transfer, respectively the occurrence of the cascade effect, is not prevented.

Besides the respective essential fluorescent or phosphorescent dyes and/or pigments, the constitution and composition of MAT1 and MAT2 is not particularly limited insofar as the radiative or non-radiative transfer of phosphorescent emission energy from the phosphorescent pigment in MAT1 to excite the fluorescent dye or pigment in MAT2 is not completely inhibited. This means that typically MAT1 and MAT2 will contain other components besides the phosphorescent pigment and the fluorescent dye or pigment, respectively.

The content of the phosphorescent pigment in MAT1 and the fluorescent dye or pigment in MAT2 is not particularly limited and may, as an upper limit, be as high as 80% by mass or less or 50% by mass or less, respectively, relative to the total mass of MAT1 or MAT2, respectively. It may preferably be 40% by weight or less, 35% by weight or less, or 30% by weight or less.

The lower limit of the content of the fluorescent dye or pigment in MAT2 and the phosphorescent pigment in MAT1 is limited in practice by the need to obtain a measurable emission signal from the fluorescent dye or pigment in MAT2 as induced by the radiative or non-radiative energy transfer from the phosphorescent decay of the phosphorescent pigment in MAT1, and is generally 1% by weight or more, preferably 5% by weight or more, and further preferably 10% by weight or more, for each of the fluorescent dye or pigment in MAT2 and the phosphorescent pigment in MAT1.

In an embodiment of the present invention, both MAT1 and MAT2 are inks. These may also be referred to as INK1 and INK2 in the following, wherein INK1 corresponds to MAT1 and INK2 corresponds to MAT2.

INK1 and INK2 may be selected from a wide variety of ink types.

Preferably, INK1 is an ink suitable for gravure or screen printing or any other printing techniques that tolerate larger particles sizes of 10 micron or more in order to allow the use of large phosphorescent pigments having such a size. It may also be an ink for offset, intaglio, flexographic, offset or pad printing. INK1 preferably has a viscosity of greater than 50 mPa sat 20° C.

The composition of INK1 typically comprises or consists of the phosphorescent pigment and one or more ink components. These include at least a binder and a solvent.

The binder in INK1 is typically an organic compound of oligomeric or polymeric nature, preferably having polar groups such as hydroxyl groups, carboxylic acid groups and esters thereof, and more preferably of the (meth)acrylate type. The binder is preferably cross-linkable by active species, such as radicals, or by application of heat.

In one embodiment, the solvent of INK1 is a non-aqueous solvent, more preferably an aprotic solvent, and even more preferably selected from the group consisting of hydrocarbons (e.g. toluene, hexane, cyclohexane), esters (e.g. ethyl acetate), ethers (e.g. THF), ketones (e.g. MEK) and mixtures thereof. Preferably, the solvent of INK1 is an ether-alcohol derivative, like for example 2-Butoxyethyl acetate.

In another embodiment, the solvent can be water, a water-miscible solvent or a mixture of water and a water-miscible solvent, such as water/ethanol mixture. INK1 may additionally also contain one or more optional ink components, such as a crosslinking or curing agent, a filler or extender (typically of inorganic nature, such as calcium carbonate), an antifoam agent and/or a polymerization inhibitor. Suitable materials are well known to the skilled person and can be suitably selected. Although this is not preferred, INK1 may also contain other coloring agents, such as fluorescent or non-fluorescent dyes and pigments.

INK2 is preferably an ink that is suitable for inkjet printing, which implies the absence of particles having size exceeding 1/10 of inkjet nozzle diameters. In consequence, particles having a size of 10 micron or more are preferably completely absent, and more preferably particles having a size of 5 micron are preferably completely absent. For the same reason, the fluorescent dye or pigment having $\lambda 2e$ and $\lambda 2a$ in INK2 is preferably a dye.

INK2 is preferably selected from inks suitable or adapted for continuous inkjet printing and drop-on-demand inkjet printing. Such inks include, besides the fluorescent dye or pigment having $\lambda 2e$ and $\lambda 2a$, at least a solvent and a binder, and preferably have a viscosity of 5 mPa s or less.

The binder may be selected from the binders described above for INK1, with binders having a polar groups being preferred. The solvent can also be selected from those described above for INK1. INK2 may also be an aqueous ink comprising water as the single solvent or in combination with other water-miscible solvents.

In addition to the binder and solvent, also INK2 may contain further optional ink components, as outlined above for INK1, such as a crosslinking or curing agent, a filler or extender (typically of inorganic nature, such as calcium carbonate), an antifoam agent and/or a polymerization inhibitor.

As described above, INK2 comprises at least one fluorescent dye or pigment having wavelength regions $\lambda 2e$ and $\lambda 2a$ that allow obtaining the cascade effect in cooperation with the phosphorescent pigment in INK1 having the wavelength regions $\lambda 1e$ and $\lambda 1a$ in the areas of spatial overlap of INK1 and INK2. INK2 may further comprise one or more additional fluorescent, phosphorescent or non-luminescent dyes or pigment. If luminescent, these should preferentially not have excitation wavelength regions overlapping with $\lambda 2e$.

Although MAT1 and MAT2 may each contain further dyes and pigments, which may or may not be phosphorescent, fluorescent or non-luminescent, MAT1 and MAT2 are different materials, i.e. do not have the identical composition.

In a preferred embodiment, MAT1 does not contain a phosphorescent material other than the one pigment having $\lambda 1e$ and $\lambda 1a$, and further preferably MAT1 does not contain a luminescent (i.e. phosphorescent or fluorescent) material other than the one phosphorescent pigment having $\lambda 1e$ and $\lambda 1a$. The same applies analogously to MAT2, so that MAT2 preferably does not contain a fluorescent material other than the dye or pigment having $\lambda 2e$ and $\lambda 2a$, and further preferably does not contain a luminescent material other than the dye or pigment having $\lambda 2e$ and $\lambda 2a$. In this case, the emission response obtained by the cascade effect can be easier identified, as it is not complicated by emissions/absorptions from other luminescent species.

However, in another embodiment, MAT1 and/or MAT2 may contain other luminescent materials than the phosphorescent pigment having $\lambda 1e$ and $\lambda 1a$ in MAT1 and/or the fluorescent dye or pigment having $\lambda 2e$ and $\lambda 2a$ in MAT2. For instance, MAT1 may comprise two or more phosphorescent pigments having overlapping or non-overlapping excitation wavelength regions $\lambda a$ and overlapping or non-overlapping emission wavelength regions $\lambda e$. If two or more pigments are selected that emit at wavelengths both falling within the excitation wavelength region $\lambda 2a$ of the fluorescent dye or pigment in MAT2, but which have different phosphorescence decay times, a unique time-dependent emission intensity behavior can be obtained. This not only depends on the types of phosphorescent pigments used in MAT1 and the type of fluorescent dye or pigment in MAT2, but also on the ratio of the phosphorescent pigments in MAT1 and their respective decay times.

Similarly, one may consider an embodiment wherein MAT1 comprises two phosphorescent pigments having different overlapping or non-overlapping emission and/or excitation wavelength regions $\lambda 1e$, $\lambda 1a$, $\lambda 1'e$ and $\lambda 1'a$, and wherein MAT2 comprises two fluorescent dyes or pigments having the respective excitation and emission wavelength regions $\lambda 2e$, $\lambda 2a$, $\lambda 2'e$ and $\lambda 2'a$ (wherein $\lambda 1e$ and $\lambda 2a$ satisfy the criteria for a cascade effect to occur, and the same applies to $\lambda 1'e$ and $\lambda 2'a$). If the phosphorescent decay times of the two phosphorescent pigments in MAT1 have different decay times, the emission caused by the cascade effect originating from the energy transfer from the phosphorescent pigment having the shorter decay time will disappear quicker than the emission caused by the cascade effect originating from the phosphorescent pigment having the longer decay time. In cases where $\lambda 2e$ max and $\lambda 2'e$ max (i.e. the maxima of the emissions of the two fluorescent dyes or pigments in MAT2) are different, a time-dependent change of the emission wavelength (colour) of the material is obtained.

Above an embodiment is described wherein MAT1 and MAT2 are each inks (INK1 and INK2, respectively). The present invention is, however, not limited to such embodiments. In an alternative embodiment, MAT1 or MAT2 may be substrate material (i.e. within the bulk of the substrate), and the other one of MAT1 and MAT2 is an ink provided on the surface of the substrate. For instance, MAT1 may be a substrate material, such as paper, cardboard or a transparent or translucent polymeric material, in which the phosphorescent pigment having $\lambda 1a$ and $\lambda 1e$ is dispersed, and MAT2 is an ink, preferably an inkjet ink, which is printed on the substrate/MAT1 such as to cover the substrate partially or completely. In this case, the substrate material/MAT1 may also be an adhesive label onto which subsequently INK2 is applied by printing or spraying. An analogous arrangement with MAT2 being the substrate and MAT1 being the ink is equally possible and envisaged in the present invention. If MAT1 and MAT2 are not inks, the necessary components (phosphorescent pigment and fluorescent pigment or dye) can be dispersed in the material forming MAT1 or MAT2 by conventionally known techniques, e.g. by adding the components to a resin prior to extrusion or casting for forming a substrate, or by adding the components to a papermaking slurry.

Interaction Between MAT1 and MAT2

Without wishing to be bound by theory, it is believed that the cascade effect occurs to a major degree at or close to the boundary between MAT1 and MAT2. In order to allow for an efficient energy transfer from the phosphorescent decay of the phosphorescent pigment in MAT1 for exciting the fluorescent dye or pigment in MAT2, the pigments, respectively the pigments and the dye, need to come reasonably close to each other. Accordingly, it is preferred in the present invention that MAT1 and MAT2 are provided adjacent to each other in z direction. It should be noted that a substrate is assumed to have a predominantly two-dimensional extension, preferably planar, that is describable by coordinates referred to as x,y, and that the third direction (third dimension) perpendicular thereto and connecting the two opposing surfaces of the substrate is referred to in this description as the z direction. An example is shown in FIG. 1.

A more prominent effect can thus be achieved if INK1 and INK2 are used and these are printed over each other, and wherein the solvent system of one of the inks is capable of at least partially dissolving the other ink. In such a case, the ink layers mix at the interface to some extent, thereby allowing the pigments, respectively the pigment and the dye, in INK1 and INK2 to come close to each other, thereby improving the efficiency of the cascade effect.

In the following, some explanations will be given for an embodiment wherein MAT1 and MAT2 are INK1 and INK2, respectively. Yet, the same considerations also apply if MAT1 and MAT2 are not inks, but e.g. one of them is another material.

It is a requirement of the present invention that the areas occupied by MAT1 and MAT2 in the security element of the present invention overlap partially or fully. An example of full overlap is given in FIG. where 101 indicates a substrate, MAT1 is INK1 and forms a patch or logo 102 (here in the form of a star), and MAT2 is INK2 and is present in the exemplary form of a dot matrix code 103. There are areas of INK1 (the star) where no INK2 is provided, but there is no area wherein INK2 (the dot matrix code) is provided, but wherein no INK1 (the star) is provided. This is an example of a "full overlap" in the sense of the present invention.

In the embodiment shown in FIG. 1, MAT1 is INK1 and is formed first, i.e. beneath MAT2/INK2 and on the substrate. That is, a substrate (e.g. paper or cardboard) is provided, MAT1/INK1 comprising the phosphorescent pigment is provided first, and MAT2/INK2 comprising the fluorescent dye or pigment is provided on top of MAT1/INK1 (with a full overlap in FIG. 1, but also partial overlap is possible in the present invention). In consequence, MAT2 is provided on top (in z direction) of MAT1. Such an arrangement may be chosen not only for inks, but for all kinds of materials MAT1 and MAT2.

The present invention is however not limited to such an arrangement, as MAT2 (comprising the fluorescent dye or pigment) may also be provided beneath MAT1 (comprising the phosphorescent pigment). However, since in this case the fluorescence emission from MAT2 used for authentication purposes has to cross the layer formed by MAT1 in order to exit the security element and to reach a detector, generally preferred is an arrangement wherein MAT1 comprising the phosphorescent pigment is formed directly on the substrate (or wherein MAT1 is or is comprised in the substrate), and wherein MAT2 comprising the fluorescent dye or pigment is formed directly on MAT1. If the alternative arrangement is chosen, i.e. wherein MAT2 is the lower layer and closer to the substrate (or wherein MAT2 is the substrate) and wherein MAT1 is provided on top of MAT2, it is preferred that MAT1 is substantially translucent or transparent with a light transmission at λ2e of 60% or more, preferably 80% or more, at the thickness employed for the security element, in dry state.

For MAT2, the material is preferably also translucent or transparent with a light transmission at λ2e of 60% or more, preferably 80% or more, at the thickness employed for the security element, in dry state, in order to avoid quenching of the emission in the material. Further, in particular—but not exclusively—if MAT2 is provided above or on top of MAT1, MAT2 is preferably also translucent or transparent with a light transmission at λ1a of 80% or more, preferably 90% or more, at the thickness employed for the security element, in dry state, in order to allow efficient excitation of the phosphorescent pigment in MAT1.

In FIG. 1, the two patterns, i.e. the star 102 and the code 103 in the example, can be applied sequentially to produce the security element. It is an advantage of the invention that the emission obtained from the area of overlap (i.e. where the cascade effect occurs) depends not only on the excitation wavelength and on the composition of the two inks in terms of dye or pigment type and concentration, but also on the overall formulation of the two inks. In particular, the composition of the inks (resin and solvent, or UV curable resin) and the printing parameters such as ink application amount will directly impact the properties of the obtained print, such as the dry material content, the thickness of the print, the distribution of pigments in the cross section of the print layer (along the Vertical z axis) and hence the final concentration of dyes and/or pigments at the interface or boundary between INK1 and INK2. It is at this interface or boundary that a significant proportion of the cascade effect is produced, and the intensity of the fluorescent emission from INK2 caused by the cascade effect will hence depend on the properties of this interface.

There is therefore an additional challenge for any counterfeiter to mimic the exact interaction in the overlap area of INK1 and INK2, which resides in the requirement to reproduce not only the two ink compositions to obtain the cascade effect with suitable dyes and/or pigments at the specific irradiation wavelength, but also to adapt the formulations in such a way that the dry material content and the interface between the two ink layers in the overlap possess the same energy transfer properties.

Also the printing methods have a significant impact on how the two ink layers will interact at the interface. In a particular embodiment of the invention, two different application methods for the two distinct patterns are used. It is an additional advantage of the invention that the response—and hence the feature used for authentication—will also depend on the ink application methods employed.

With respect to the ink formulation, the combination of
1) the solvent used to print the secondly applied ink (SOLVENT T2) and
2) the type of resin or varnish or any other material which will form the solid dry material from the formulation of the firstly applied ink (RESIN T1)

has a substantial impact on the efficiency of the cascade effect at the ink layers' interface in the overlap region for the following reason. Here, and also in the following, a component denoted with T1 or T2 represents a component of the material applied firstly (T1) or secondly (T2). Yet, material applied firstly (T1) may be either of MAT1 and MAT2, The material applied secondly (T2) it then the respective other material.

In case that RESIN T1 cannot be dissolved by SOLVENT T2, or in the case where RESIN T1 is densely packed so it does not allow the secondly applied ink to diffuse into the interface with the firstly applied ink, the interface will show an abrupt or sharp transition from MAT1 to MAT2, and the energy exchange between the phosphorescent pigment and the fluorescent dye or pigment will not be favorable to the cascade effect because only a few of them will be close to the others.

On the other hand, if SOLVENT T2 can dissolve partially RESIN T1 at the interface, or if RESIN T1 is porous enough to let the secondly applied ink diffuse into the firstly applied ink, an intermediate region will be formed. Here, the phosphorescent pigment in INK1 and the fluorescent dye or pigment in INK2 will come closer to each other, so that the average distance between the two is reduced for a significantly larger amount thereof. This enhances the efficiency of the cascade effect. Note that it is advantageous that RESIN T1 is freely miscible with RESIN T2, i.e. that no phase separation between the two occurs. This can be achieved by using the same or chemically similar materials as RESIN T1 and RESIN T2.

Therefore, the formulations of INK T1 and INK T2 are preferably such that INK T1 is a solvent based ink providing a relatively porous print and that SOLVENT T2 is able to dissolve RESIN T1 to a certain extent and diffuse within the ink layer formed first.

There is another factor that influences the proximity of the donor and acceptor dyes or pigments and hence the efficiency of the cascade effect. In particular, in cases where INK1 contains donor pigments, which are typically solid, isolated and non-soluble grains of phosphorescent material, there is an additional challenge for the ink formulation to provide the acceptor dye or pigment close to the donor pigments. For an efficient energy transfer, not only the concentration of the phosphorescent pigment in INK1 within the dry ink layer should be sufficient, but also the position of these (at the surface or uniformly distributed within the layer) is critical and can be controlled by ink formulation. This is an additional lever to tune the efficiency of the cascade effect that can be exploited in the invention, as again a counterfeiter would have to mimic not only the components employed, but also their interaction, as influenced by the arrangement of the components at the interface. These effects are also demonstrated in the Example provided at the end of the specification.

In the following, embodiments of the invention are described with reference to the Figures.

As shown in FIG. 1, a label or product 101 is printed with a background print (also referred to as patch or logo) 102 using a first ink (INK1) containing a phosphorescent pigment. Optionally, the background print (patch or logo) can be printed with INK1 directly on product packages or on documents, or furthermore on the products themselves, where possible. The patch or logo 102 may also be part of the package, e.g. by using a cardboard or plastic material wherein the phosphorescent pigment is dispersed.

Then, a pattern 103, which can in principle be chosen in any suitable or desirable way and is shown in the Figure by way of example as a dot matrix code, is printed on top of this patch or logo 102 using a second ink (INK2) containing a fluorescent dye or pigment. In this embodiment, MAT2 is INK2 in the form of a code. However, MAT2 may also take the form of other codes, indicia, letters, or other patterns, such as spray patterns. The pattern formed with MAT2 may include item-specific or product-specific information in encoded or non-encoded form, such as a serial number. Typically, INK2 is applied in a coding center or packaging line during personalization of the labels or products, as in a usual process.

According to FIG. 2, the phosphorescent pigment contained in INK1 is selected such that its phosphorescent emission range $\lambda 1e$ overlaps with the excitation range $\lambda 2a$ of the fluorescent dye or pigment in INK2 used to print the pattern 103 in order to obtain the cascade effect.

With continuous illumination in the excitation range $\lambda 1a$ of the background print 102, the phosphorescent pigment is excited and emits phosphorescence within a wavelength range $\lambda 1e$. This emission excites the overlaying pattern 103 by a cascade effect. Due to the phosphorescent nature of the phosphorescent emission (i.e. due to the long decay time), this phosphorescent emission persists partially after illumination cutoff. In consequence, also the code printed from INK2 continues to fluoresce faintly after illumination cutoff (delayed lifetime), as still phosphorescent emission occurs that excites the fluorescent dye or pigment.

Optionally, the code 103 can separately be detected and decoded as usual with illumination in its excitation spectral range $\lambda 2a$ with good contrast, because measurement is not compromised by the background phosphorescent background print 102, which is typically insensitive to this illumination ($\lambda 2a$ is not able to excite phosphorescence of the background print 102).

The less intense emission from the dot matrix code 103 in the afterglow, i.e. after the illumination within the wavelength region $\lambda 1a$ is ended, is caused by the phosphorescent emission in the range $\lambda 1e$ overlapping with $\lambda 2a$, which lasts significantly longer than any fluorescent emission. This continuing emission is detected and confirmed by suitable image processing techniques, e.g. techniques that will be explained in more detail in connection with FIGS. 3a and 3b.

Figure 4:
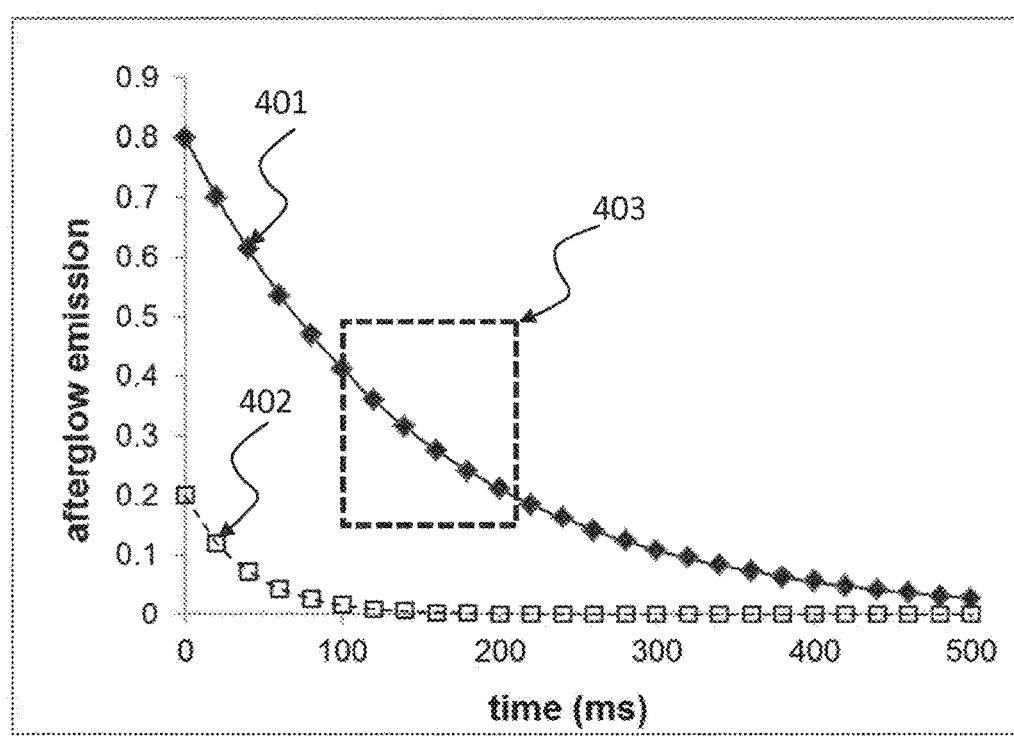
FIG. 4 illustrates an example of time evolution of the afterglow emission induced by the cascade effect of a genuine mark on a long afterglow background compared to a non-genuine mark consisting of a fluorescent code printed onto a background not producing an afterglow cascade emission.

The mark is authenticated by evaluating a feature associated with the presence of the cascade effect and the presence of phosphorescent emission. This can e.g. be the decay time of the remaining faint afterglow emission in $\lambda 1e$ wavelength range, in a specific time range. By comparing this decay time with a predetermined level, the security element can be identified as genuine or non-genuine (see FIG. 4). In FIG. 4, 401 identifies a genuine mark, 402 identifies a non-genuine mark, and 403 represents a comparison window in time and an emission intensity representing an authentication rule, e.g. in such a way that if the measured intensity values fall into the window, the mark is authentic, and if a predetermined threshold number of measured intensity values falls outside of the window, the mark is judged as inauthentic.

This method provides a unique, non-standard, authentication feature which enhances security, remains covert and is difficult to reverse engineer or imitate. In a preferred embodiment, the fluorescent pattern of MAT2 (e.g. code 103 of FIG. 1) remains invisible to the naked eye even if the phosphor patch can be made visible by e.g. UV-VIS illumination (i.e. illumination in electromagnetic wavelength ranges from the UV part of the spectrum to the visible part of the spectrum). Furthermore even if either the security ink to print the fluorescent pattern of MAT2 is imitated or stolen, or the pre-printed labels comprising MAT1 are stolen, the security mark of the present invention cannot be completely forged, as the security feature resides in the presence of both elements in a specified relationship.

Arrangement and Shape of MAT1 and MAT2

The shape and arrangement of MAT1 and MAT2 are not particularly limited, as long as there is at least one area wherein MAT1 and MAT2 overlap and allow a cascade effect to occur. There may be cases where a part of the area occupied by MAT1 does not overlap with the area occupied by MAT2, and wherein also a part of the area occupied by MAT2 does not overlap with area occupied by MAT1 (partial overlap). For instance, if two intersecting circles of the same diameter and line width made from MAT1 and MAT2, respectively, are present, a partial overlap in the intersection areas is present, whereas the non-intersection area of one of the circles is made only from MAT1, and the non-intersection area of the other circle is only made from MAT2.

The areas of MAT1 and MAT2 may however also overlap fully. This is for instance shown in FIG. 1, where MAT2 (the dot matrix code 103 made from INK2) is present only in areas where also MAT1 is present.

In the simplest arrangement, MAT1 and MAT2 define solid areas (e.g. rectangular) that overlap partially or fully. The shape or pattern of the areas associated with MAT1 and MAT2 may, however, also comprise or encode any suitable or desirable information, such as in the form of words, letters, numbers, logos or indicia. Also, only one of MAT1 and MAT2 may define such information. One example of such an arrangement would for instance be the letter "A" made from one of MAT1 or MAT2, wherein the short central line connecting the two long lines is an area of overlap, i.e. wherein the respective other material is additionally present. Upon sufficient excitation within the wavelength region $\lambda 1a$, a cascade effect afterglow will be observed after illumination cut off in the area of overlap, i.e. the short line connecting the two long lines in the letter "A".

In preferred embodiments, one of MAT1 and MAT2 provides a product-specific or item-specific code, such as a barcode, serial number, or manufacturer's identity code. The respective other material can be incorporated into the substrate on which the code is provided, or can be a patterned or solid area (or print) beneath or above the code. This patterned or solid print may also provide encoded or non-encoded information. By applying such an arrangement, the area in which the code is subsequently provided (containing either MAT1 or MAT2) can be provided at a first place, e.g. a principle manufacturing site, and the code (containing the respective other material) can then be provided at another place, e.g. the place of final assembly. This provides a physical link between different places, and can hence be used to provide a link for e.g. being able to trace a product along a chain of manufacture.

In other embodiments, MAT1 and/or MAT2 may be invisible to the naked eye under standard illumination (e.g. sun light or standard room lighting), at least in their final form when applied to the product to be protected by the security element of the present invention (providing e.g. a colored background). This provides a covert security feature that can only be detected under specific illumination conditions, e.g. when illuminated by UV. This can be achieved by using a phosphorescent pigment in MAT1 having $\lambda 1a$ in the range.

In yet another preferred embodiment of the present invention, $\lambda 2e$ does not fall within the visible light range. If $\lambda 2e$ falls e.g. within the IR range, the occurrence of the cascade effect can only be observed by a spectral analysis including this range and using illumination conditions including $\lambda 1a$. If for instance $\lambda 1a$ falls in the UV range and $\lambda 2e$ falls in the IR range, spectral analysis in the IR using illumination including UV is necessary in order to detect the security element. This provides a very covert security element that will not be easily detectable for counterfeiters.

In other embodiments, MAT1 or MAT2 may be used in forming an item-specific code, such as a serial number provided with full or partial overlap over the respective other material. The item-specific code may also be a unique but random pattern, such as a spray pattern, that is stored in a database and can identify a specific product.

Authentication Method and Apparatus Therefor

Figure 3A:
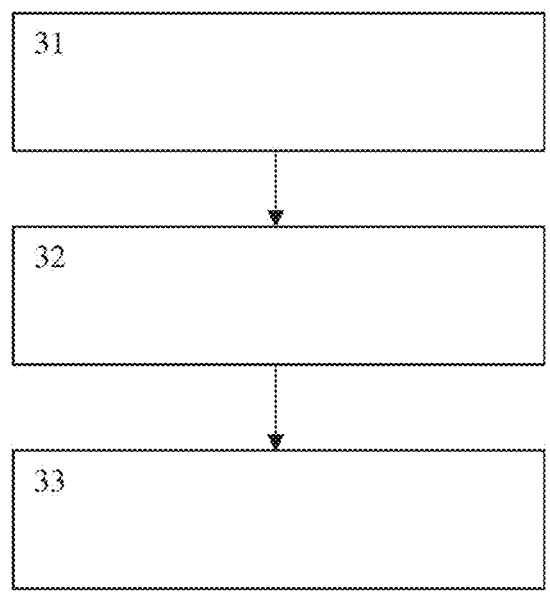

A method for authenticating a security element of the present invention may comprise the following steps, which are illustrated in the flow chart of FIG. 3a:
  i. irradiating the security element with a light source in the wavelength range $\lambda 1a$ for a given time to excite the phosphorescent pigment in MAT1 to emit phosphorescence radiation in the wavelength range $\lambda 1e$ (step 31);
  ii. after the given time has elapsed, subsequently detecting a response emitted from a region of a spatial overlap of MAT1 and MAT2 in the security element within the wavelength range $\lambda 2e$ (step 32), and
  iii. judging the authenticity of the security element on the basis of the response in the wavelength range $\lambda 2e$ (step 33).

The "given time" in step i. needs to be sufficient to induce phosphorescent emission in the wavelength region $\lambda 1e$. In this sense it may be understood as a "pumping", "charging" or "loading" step, i.e. it serves to supply the energy to the phosphorescent pigment in MAT1, so that an emission in the emission wavelength region $\lambda 1e$ of magnitude and duration sufficient for inducing the cascade effect and allowing detection by the chosen detection system becomes possible. The duration of irradiation is variable and depends on the light source irradiance and the phosphorescence efficiency. It can be determined by measuring the phosphorescence emission intensity as a function of time, which shows a typical increase until it saturates. An irradiation time producing at least 60 to 80% of the saturation emission level can be considered sufficient to produce the desired effect (the phosphorescent effect will be obtained long enough for authentication purposes). This "given time" is thus usually a time of 0.1 seconds or longer, more preferably 0.5 seconds or longer, and more preferably 1 s or longer. While the "given time" has no specific upper limit, it is preferably 10 seconds or less, more preferably 5 seconds or less, in order to allow for a rapid authentication.

The light source used in step i. is not particularly limited, as long as it emits electromagnetic radiation within the wavelength region $\lambda 1a$. Accordingly, it may be necessary to select the light source in accordance with $\lambda 1a$, as can easily be accomplished by a person skilled in the art. The light source may e.g. by an LED or a laser.

The irradiance of the irradiation in step i. should be sufficient to cause a detectable cascade effect. While there is no specific upper limit to the illumination intensity, it is preferably 1 mW/cm$^2$ or more as measured on the surface of the security element.

The detection of the emission in the wavelength region $\lambda 2e$ after the end of the illumination can be achieved by using conventional detection technology. Preferably, a band pass filter is employed to selectively detect the emission in the wavelength region $\lambda 2e$.

Step iii, can be performed in any suitable or desirable way, e.g. in a processing unit and it may relate the measured emission, e.g. its intensity or intensity-time behavior, to the time after the given time of the illumination in step i has elapsed.

According to an embodiment of the invention step iii. comprises a sub-step iii.a of extracting a value related to at least one parameter associated with the emission in the wavelength region $\lambda_{2e}$, and a sub-step iii.b of determining whether the extracted value corresponds within a certain level of confidence to a value that is characteristic for an authentic security element. The parameter may e.g. be associated with the intensity of the observed emission. The specifics can be chosen in any suitable or desirable way, e.g. the signal level of the emission in the wavelength region $\lambda_{2e}$ a specific time after the elapse of the given time of irradiation in step i may be compared with a stored comparison value, or the value of the signal level averaged over a specific time after the elapse of the given time of irradiation in step i may be compared with a stored comparison value.

According to a further embodiment of the invention, the parameter is associated with the decay time of the phosphorescent pigment in terms of exponential decay according to $e^{-t/\tau}$, where t denotes time and $\tau$ is a decay constant. The specifics can again be chosen in any suitable or desirable way, e.g. the observed signal of the emission in the wavelength region $\lambda_{2e}$ may be analyzed with respect to time to extract a decay factor τ(measured), which is then compared with a reference decay constant τ(reference) associated with an authentic mark.

Naturally, step iii my comprise determining values related to a plurality of parameters associated with the emission in the emission wavelength region and then comparing the respective values with respective reference values and judging authenticity in dependence on the result of the comparison.

Due to the specific decay time of the phosphorescent pigment and the combination with a fluorescent dye or pigment, in combination with the specific composition and application method of MAT1 and MAT2, a very exact and very distinctive design of the security element is possible, as described above and demonstrated in the examples. Thereby, it is possible to provide a security element of high distinctiveness that is hard to falsify. In other words, the determination of a security element as genuine, or the detection of forged security elements in case that the observed behavior does not conform to expected (pre-stored) reference values or ranges of values, becomes very reliable. The observation of the overlap area between MAT1 and MAT2 can be done in any suitable or desirable way. For example, an embodiment of the present invention may additionally comprises steps for acquiring an image of the security element in the wavelength range λ2e upon illumination in the wavelength range λ2a, and processing the acquired image, e.g. for extracting a pattern such as dot-matrix code contour from the mage, by for example an image thresholding technique. This, however, is an optional step. Furthermore, the image processing may comprise generating and processing a digital correlation mask from the image.

Specific embodiments of the authentication method of the present invention embodying one or more of the above principles are also illustrated in the examples and in FIGS. 3b, 4, 7, 8, 9 and 10, which will be described further on.

FIG. 3b shows as an example of the present invention a flow diagram of a generic image acquisition and authentication scheme using image processing.

In step 301 an image of the pattern (e.g. 103) is taken with illumination in the $\lambda_{2a}$ wavelength range. Then, in step 302, the contour of the pattern may be extracted with, for example, an image thresholding technique. Finally, a mask for later image processing purposed may be generated in step 303. In step 304 illumination in the λ1a wavelength range is applied for a sufficient time to load the phosphorescent pigment in MAT1, such that a sufficiently long and strong afterglow is generated, as explained above in connection with step i of FIG. 3a. In step 305 it is determined that the sufficient time for loading the phosphorescent pigment has elapsed, and consequently the illumination in the λ1a wavelength range may be terminated, and then a plurality of time sequential images of the pattern in the afterglow are taken.

In step 306 image processing is applied on the plurality of pictures. This image processing may make use of the mask generated in step 303. For example, a matching of the mask representing the pattern with the images taken in step 305 is performed, in order to identify the areas in said images that correspond to the pattern. This can be done in any suitable or desirable way, e.g. with the help of a correlation mask method that will be described further on in connection with FIG. 8.

Step 307 comprises extracting afterglow emission characteristics with respect to acquisition time, as e.g. described above in connection with steps iii, iiia. Finally, step 308 comprises judging whether the mark is authentic from a predetermined rule on the time evolution of the afterglow emission characteristics, as described above in connection with steps iii, iiib.

It should be noted that the example of FIG. 3b may be varied in many ways. For example, steps 301-303 could be omitted. As an example, an image processing reference mask may be pre-stored, e.g. in the event that the pattern under examination is of predetermined form. Alternatively, step 301 may be changed to use the λ1a illumination (thereby making the provision of an illumination source for the λ2a wavelength range unnecessary) and steps 301-303 can then be performed in parallel to step 304 by imaging and thresholding under the λ1a illumination.

Figure 7:
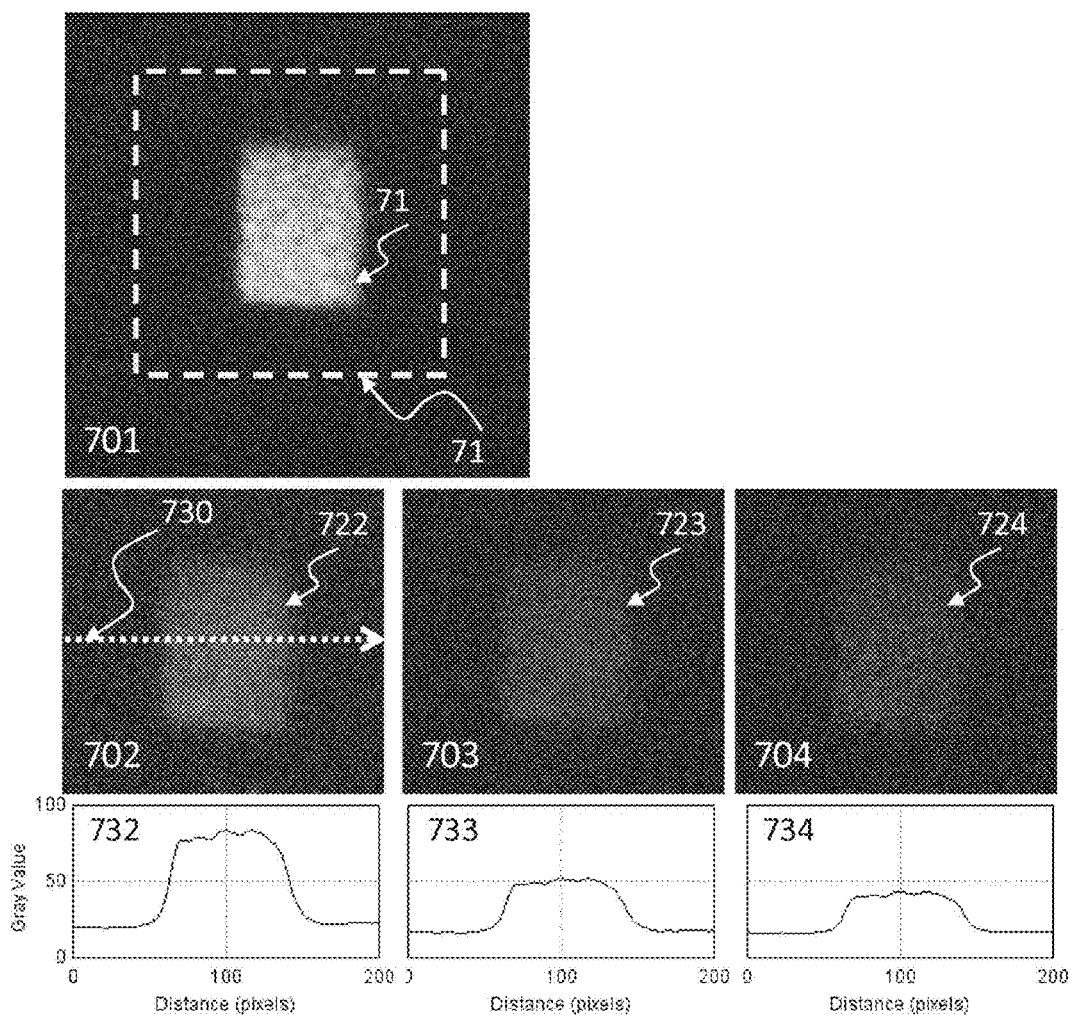
FIG. 7 shows an image 701 of the mark of a detailed example of the invention when irradiated with radiation from a deep blue LED and the region in dotted line where correlation is applied. Also represented in this figure is a sequence of consecutive images (702, 703, 704) along with their pixel intensity profiles, taken in the afterglow.

FIG. 7 shows results of an example process of the described kind 701 shows an actual image of an example mark during excitation with deep blue light (e.g. variation of step 301 of FIG. 3b) and 702-704 show images acquired at various delays after deep blue excitation cut-off showing afterglow cascade emission (step 305 of FIG. 3b), i.e. image 702 at 206 ms delay, image 703 at 412 ms delay, and image 704 at 618 ms delay 732, 733 and 734 indicate intensity profiles of images 702, 703, 704 respectively along the line 730. Contour 710 on image 701 shows the region where a correlation function is applied.

An authentication apparatus of the present invention is adapted for authenticating the security element of the present invention in accordance with the method of the present invention. In consequence, the present invention also includes the use of the authentication apparatus for determining the authenticity or non-authenticity of a security element, wherein the authenticity is determined based on the occurrence of the cascade effect and the time-dependent emission in the wavelength region λ2e after cut-off of the illumination including λ1a.

Figure 11:
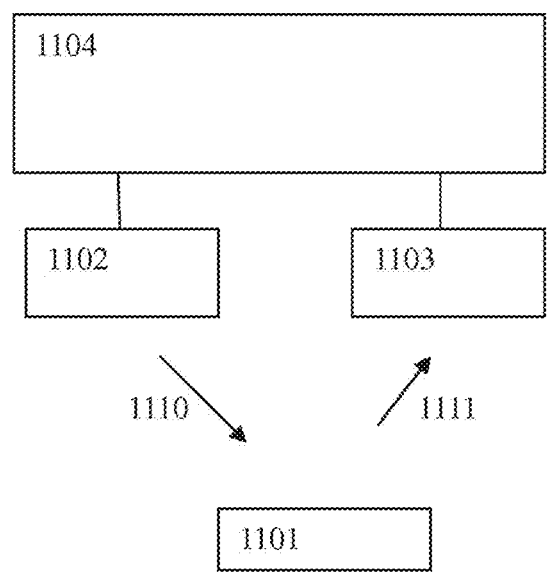
FIG. 11 shows a schematic representation of an authentication apparatus according to an embodiment of the present invention.

The apparatus comprises at least a radiation source for performing step i capable of emitting in the wavelength region λ1a, a detector for performing step ii capable of detecting radiation in the wavelength region λ2e, and a processing unit for performing step iii, wherein the processing unit may e.g. verify whether the observed emission within the wavelength range λ2e falls within a predetermined set of rules for determining if the security element is authentic. A schematic representation of such an apparatus is shown in FIG. 11. Reference numeral 1102 relates to a radiation source that can emit radiation 1110 in the wavelength region λ1a for irradiating a security element 1101, e.g. an LED or a laser device, 1103 represents a detector for receiving radiation 1111 from the element 1101, e.g. an imaging camera, and 1104 stands for a processing unit, e.g. a programmable control device that has control programming for controlling the source 1102 according to step i and the detector 1103 according to step ii, and which has image and data processing programming arranged for performing the judgment of step iii.

In a preferred embodiment, the authentication apparatus comprises
  a first radiation source emitting substantially in the wavelength range λ1a for irradiating the phosphorescent pigment in MAT1;
  optionally, a second radiation source emitting substantially in the wavelength range λ2a for irradiating the fluorescent dye or pigment in MAT2,
  an imager selectively sensitive in the wavelength range λ2e for capturing images of the security element;
  a computing device for storing and processing the captured images under the first and second irradiation sources and after the second radiation source cut-off and for comparing the processed image result with a set of pre-defined stored rules to judge if the security element is authentic, and optionally, a decoder engine to decode information in a digital code, e.g. the information contained in a dot-matrix code, for example for further identification of the products carrying the security element.

Example 1

In order to demonstrate the invention, several marks composed of a phosphorescent print made from INK1 with digitally printed codes or logos on top made from INK2 were produced (see Table 1 below).

Preparation of Long Afterglow Background Ink (INK1):

The phosphorescent pigments were incorporated in the formulation of silk screen inks based on the following blank composition:

31.5 wt.-% Tripropyleneglycol diacrylate monomer, 17.9 wt.-% trimethylolpropane triacrylate, 19.0 wt.-% EBECRYL™ 2959, 11.6 wt.-% EBECRYL™ 80, 2.1 wt.-% TEGO® Airex 900, 1.0 wt.-% GENORAD™ 20, 9.5 wt.-% Calcium carbonate, 2.1 wt.-% Benzil dimethyl ketal and 5.3 wt.-% IRGACURE® 1173. While this system is preferably used for the present invention, also other systems can be employed as long as it is ensured that there is no or very little spectroscopic or chemical interferences of the blank with the phosphorescence of the phosphorescent pigments that will be added to form MAT1 or INK1, INK1 can be obtained by adding from 1% to 30% of long afterglow phosphor to a blank silk-screen formula, e.g. the one shown above.

Two commercial phosphorescent pigments were tested and incorporated at various concentrations in the above blank: Lumilux® blue SN and Lumilux® green SN-F2Y (Honeywell). The excitation and emission spectra of these pigments are represented in FIG. 5. These spectroscopic properties were measured on samples printed with silk-screen ink composition as described above using a spectrofluorometer (Horiba Jobin Yvon Fluorolog III).

The respective INK1's were applied as solid print area by silk screen printing with a mesh of 90 T on a suitable white substrate (e.g. the white part of LENETA N2C-2 substrates), followed by standard UV drying at room temperature. The mesh is not limited to 90 T, it can be bigger or smaller, depending on the nature of the phosphorescent pigment.

Preparation of Digital Ink (INK2):

First a blank is prepared which contains typically a resin, a binder, a solvent and some additives. A composition that was found to serve this purpose well is composed of 87%-weight Methylethylketone, 10.3%-weight of a hydroxyl-containing copolymer made from 84%-weight vinyl chloride and 16%-weight of acrylic acid ester (commercially available from Wacker Chemie under the tradename VINNOL E15/40 A) and 2%-weight of a terpolymer made from 84%-weight vinyl chloride, 15%-weight vinyl acetate and 1%-weight dicarboxylic acid (commercially available from Wacker Chemie under the trade name VINNOL E15/45 M). While this system is preferably used for the present invention, also other systems can be employed as long as it is ensured that there is no or very little chemical or spectroscopic interference of the blank with the fluorescence of the dye or pigment that will be added to form INK2.

Then, INK2 is obtained by adding to the above blank 1.23%-weight of Lumogen® F Orange 240 fluorescent dye. An excitation spectrum 601 and emission spectrum 602 of a fluorescent dye (Lumogen® F Orange 240) in INK2 used for printing the digital code 103 on top of the phosphorescent background 102 in a detailed example of the invention is shown in FIG. 6. Arrow 603 indicates the wavelength range of the measuring device. FIG. 6 shows the excitation and emission spectra of this dye by measuring a dry film deposit of ink2 using a spectrofluorometer (Horiba Jobin Ybon Fluorolog III). The dry film is obtained from a wet film deposit of 12 μm thickness prepared using e.g. a K Control Coater from RK Print Coat Instruments using, e.g., the HC2 coating bar, on a suitable white substrate (e.g. the white part of LENETA N2C-2 substrates), followed by drying at room temperature.

Cascade Effect in the Case of INK1 and INK2:

By observation of the spectral properties of the phosphorescent pigments in FIG. 5 and of the fluorescent dye pigment in FIG. 6, it becomes apparent that these satisfy the conditions for a cascade effect to occur, as represented in FIG. 2. More specifically the emission spectral range of Lumilux® blue SN in INK1 (corresponding to $\lambda 1e$) extends from about 450 to 550 nm which closely matches the excitation wavelength range of Lumogen® F Orange 240 (corresponding to $\lambda 2a$) which spans over 420-540 nm. Therefore the spectral overlap between $\lambda 1e$ and $\lambda 2a$ is in the range 450-540 nm. In case of Lumilux® green SN-F2Y, the emission spectral range $\lambda 1e$ extends from 450 to 620 nm which provides also a fairly good matching, over the range 450-540 nm as well. Therefore, INK2, when printed on top of or beneath INK1, will be excited by the long afterglow phosphorescence of INK1, provided that INK1 has been excited in the spectral range $\lambda 1a$ for a sufficiently long time to be charged and to obtain a phosphorescent emission.

Sample Preparation:

The samples inventoried in Table 1 were prepared by applying successively the silk screen printed INK1 and the digitally printed code/logo using Lumogen® F Orange 240 based inkjet ink INK2 as described above. For the purpose of the example described here, INK2 was applied with a spray device (Nordson Microspray EFD Series 787MS-SS) and using a rectangular mask to mimic a dot-matrix code area 711 as shown in image 701 of FIG. 7. A similar embodiment can be achieved by using a continuous inkjet or a Drop on demand printer to print a dot-matrix code using INK2.

Various concentrations of the Lumilux® green SN-F2Y were used in order to investigate its effect on the afterglow characteristics of the marks.

TABLE 1

Properties of the samples investigated in the detailed example of the invention.

| Sample name | BG1-20% | BG2-5% | BG2-15% | BG2-30% | Fake | Reference |
|---|---|---|---|---|---|---|
| Afterglow pigment | Lumilux® blue SN | Lumilux® SN-F2Y | Lumilux® SN-F2Y | Lumilux® SN-F2Y | None | None |
| Concentration (weight-%) | 20 | 5 | 15 | 30 | NA | NA |

Image Acquisition Sequence:

Images were acquired using a luminescence imaging device composed of two light sources and a band-pass filter in front of an imaging device composed of a lens and a digital camera. The light sources can be synchronized with the frame acquisition of the camera.

The first light source emitting in the λ1a wavelength range is a deep blue LED centered at 410 nm and is capable of exciting the phosphorescent pigment of INK1 as shown by the arrow 505 in FIG. 5. Excitation of the MAT1 background can be done with deep blue visible light (350-450 nm). The second light source emitting in the λ2a wavelength range is a green LED centered at 530 nm which is capable of exciting INK2 as can be seen from the excitation curve 601 in FIG. 6. The band pass optical filter transmits in the wavelength range 550-700 nm as shown by the arrow 603 in FIG. 6. Therefore, irrespective of the excitation wavelength used, only emission 602 from Lumogen® F orange 240 in INK2 is detected.

Image 701 shown in FIG. 7 is acquired by irradiating the mark with the green LED and shows direct fluorescence of the INK2 mark 103, as represented by area 711. This corresponds to step 301 in FIG. 3b.

After this reference image 701 was acquired, the mark is irradiated with the deep blue LED for a given time in order to excite the long afterglow phosphor patch 102. This corresponds to step 304 in FIG. 3b. The duration of irradiation is variable and depends on the LED irradiance and the phosphorescence efficiency of INK1. It can be determined by measuring the phosphorescence emission intensity as a function of time, which shows a typical increase until it saturates. An irradiation time producing at least 60 to 80% of the saturation emission level can be considered sufficient to produce the desired effect (the phosphorescent effect will be obtained long enough for authentication purposes).

Once INK1 has been sufficiently excited, the irradiation may be cut off and an image sequence is acquired at different time delays subsequent to irradiation cut off. This corresponds to step 305 in FIG. 3b. Images 702, 703 and 704 in FIG. 7 represent the first 3 images of a typical sequence of the detailed example, taken at time delays of 206, 412 and 618 ms respectively; all with an exposure time of 200 ms. One can distinguish a faint emission in the regions 722, 723 and 724 respectively. This faint emission is decreasing over time as demonstrated by the emission profiles 732, 733 and 734 taken along the line 730 in the respective images. Since the deep blue LED irradiation was cut-off, these faint emission areas are witnessing the cascade excitation of INK2 by INK1, during the afterglow of the latter, which is the key object of the invention.

Image Processing Steps:

In case the cascade excitation is efficient due to high loading and high efficiency of the afterglow MAT1 background and because the fluorescent dye in INK2 has a high efficiency, the cascade-induced afterglow emission of mark 103 can directly be measured from intensity levels in regions 722, 723 and 724. From the decaying intensity level 401, as represented in FIG. 4, either a decay time constant, or an intensity-vs.-time bounding box 403 can be used as authentication feature. This requires minimum image processing, such as extracting a mean intensity level from known regions of the mark 103 in successive afterglow images.

In case where the afterglow emission of mark 103 is faint and vanishes quickly in the image noise, an image correlation technique can be used. Applying a correlation mask or so called kernel onto an image allows determining whether a significant even if low intensity level is present in the region of the mask. This is a very efficient technique to extract faint intensity levels from regions in an image which are a priori supposed to produce such faint emission.

Figure 8:
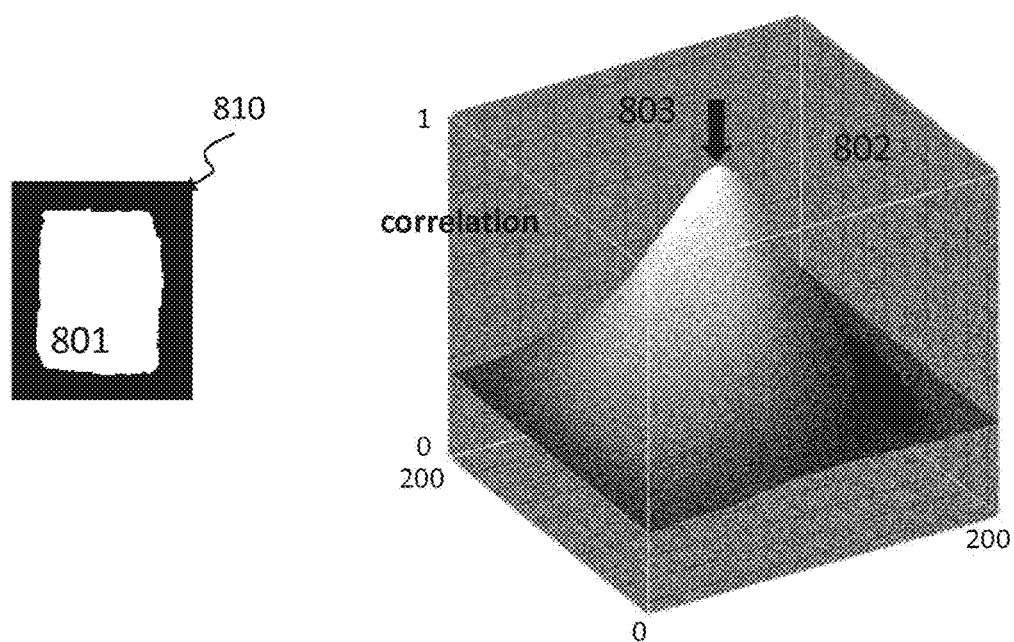
FIG. 8 schematically illustrates the concept of a correlation mask 801 extracted from image 701 and the result of this correlation mask when applied onto an afterglow image 702 used in the detailed example of the invention.

From the reference image 701, e.g. a correlation mask/kernel 801 of the mark 103 can be generated by applying an image threshold, for example an Otsu threshold, to extract only the INK2 area, and a subsequent crop to keep only the mark 103 plus a border 810 of, for example 10 pixels. This correlation kernel is a matrix (in the region 810) where pixel elements corresponding to the INK2 mark 103 have the value of 1, whereas all other elements are zero. From the reference image 701, the location of the extracted kernel 801 is recorded. The correlation kernel 801 is applied on all images acquired in the phosphorescence afterglow (e.g. images 702, 703, 704). Then a correlation value is calculated at every pixel of the correlation area 710 by shifting the kernel all over the image. A correlation matrix, represented as a 3D plot 802 in FIG. 8 shows a bell-shaped 2D intensity profile over the correlation area 710. Arrow 803 indicates the correlation value that is obtained when the kernel position matches the previously stored expected position of the mark. A ratio of correlation can be calculated by dividing the value of correlation 803 by the mean of correlation all over the area 710.

The above process corresponds to steps 306 and 307 in FIG. 3b. In a variation of the described embodiment, a correlation kernel could be extracted from an image of the mark acquired during the phosphor loading time. This would prevent from doing step 301 of FIG. 3b. Steps 302 and 303 can then be performed in parallel with step 304. Proceeding this way lead to a simpler authenticating device (one light source only) and faster authentication process.

Figure 9:
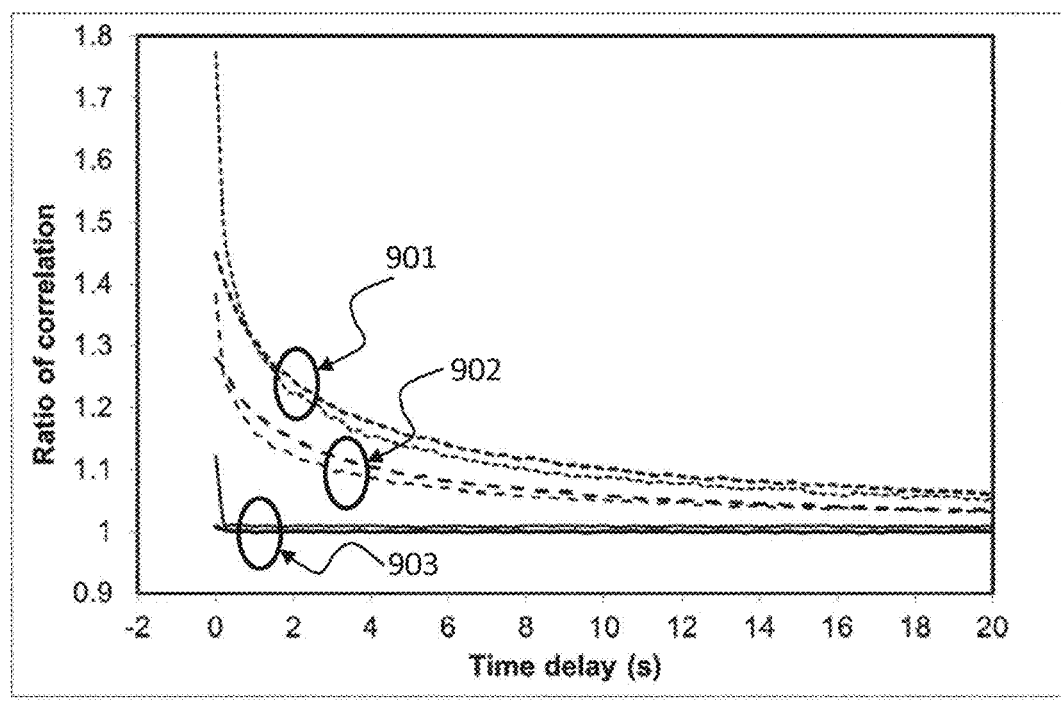
FIG. 9 shows the calculated ratio of correlation as a function of the afterglow delay time for different samples.

Authentication of the Marks:

The correlation ratio can be used as authentication feature of the mark in the invention. For example, it is calculated for every image in the afterglow and can be plotted as a function of time delay after excitation cut-off as shown in FIG. 9 for 2 different afterglow background samples of Table 1, namely 901 for BG2-15% and 902 for BG2-20%. These two correlation ratio curves are clearly decaying differently one from another and also very differently from the ones of the fake samples 903.

Figure 10:
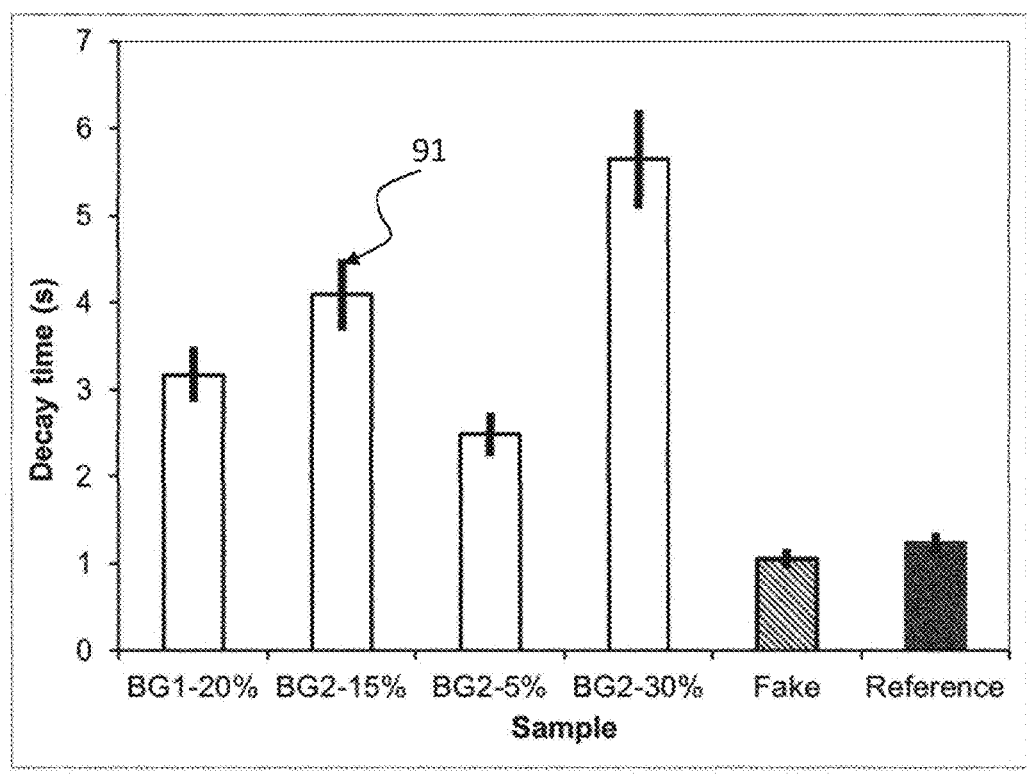
FIG. 10 shows the calculated decay time constant t of the correlation ratio in the afterglow for different backgrounds and for fake and reference samples.

Moreover a decay time constant can be extracted from the time evolution of the correlation ratio curves 901, 902 and 903. FIG. 10 shows the values of the calculated decay time constants of the respective ratios of correlation for all the samples of Table 1, i.e. calculated decay time constants of the correlation ratio for different backgrounds and for fake sample (different ink2 without afterglow background) and reference (same ink2 without background), Bars 910 represent the respective tolerances for rules based on the value of the decay time for authentication. One can clearly observe significantly different decay times for the different MAT1 backgrounds, which allows tailoring different marks that could be differentiated by their decay times. Moreover, the fake mark and the reference sample, which do not have afterglow background made from MAT1, show significantly shorter decay times which permit to distinguish them from "genuine" marks.

Authentication rules can be defined as tolerance levels 910 of FIG. 10 on the decay time. In other words, if the measured decay time falls within the tolerance range 910 then the mark can be considered as authentic provided that it is based on afterglow background BG2-15%; if the decay time falls outside the range 910 the marks is considered as not authentic.

Other authentication criteria can also be used, which are based on the value of the ratio of correlation 901 or 902 in a given time delay range, in a similar manner as was described above when afterglow intensity levels were considered (see FIG. 4).

Although above specific security elements with a specific shape and specific components in INK1 and INK2 are described, a skilled person will easily recognize that the authentication steps can be applied independently of the specific shape and composition of the security element, as long as MAT1 and MAT2 are present in partially or fully overlapping regions and the requirements for a cascade effect to occur are satisfied.

Example 2

In the following example 2, two different formulations of INK1 were tested based on the following blank properties in order to determine the effect of ink compositions on the observed cascade effect:

1) INK1 with solvent-based blank formulation (FORMULATION blank A) Where the dry inks layer is thin and hence pigments are concentrated and much of them are close to the top surface 2) INK1 with UV-curable resin blank formulation (FORMULATION blank B) where dry ink layer is significantly thicker, the pigments are homogeneously distributed along the thickness (z axe) of the print layer, and consequently, the pigment concentration at the surface of the print is reduced as compared to the solvent based ink Both of these inks blanks are used for silk-screen inks and their respective formulations are described in details below. For the example described here, two examples of INK1 using the two different blanks were formulated by adding 15%-weight of Lumilux® green SN-F2Y pigment (Honeywell) as donor. A test patch of each formulation is first silk-screen printed on a suitable white substrate (e.g. the white part of LENETA N2C-2 substrates) with a 90 T silkscreen frame, followed by solvent evaporation drying for the FORMULATION A and UV curing for the FORMULATION B.

A typical digital printing ink blank was formulated for INK2 (detailed FORMULATION C below), INK2 is obtained by adding to the blank 0.3%-weight of Lumogen® F Orange 240 fluorescent dye as acceptor.

For the purpose of the example described here, INK2 was applied with a spray device (Nordson Microspray EFD Series 787MS-SS) and using a rectangular mask to produce a distinguishable pattern on top of, and partially covering each of the two silk-screen printed patterns. The spray parameters were adjusted so as to produce a dry film equivalent to the one obtained from a wet film deposit of 12 µm thickness prepared using e.g. a K Control Coater from RK Print Coat Instruments using, e.g., the HC2 coating bar, followed by drying at room temperature.

The efficiency of the cascade effect for the 2 samples was measured with a camera equipped with a lens and a long pass optical filter to transmit mainly the fluorescence from INK2 in a wavelength range between 600 nm and 950 nm, while using a deep blue LED emitting at a peak wavelength of 410 nm for the excitation of INK1 only (INK2 is only very weakly excited at the wavelength range where the deep UV LED is emitting). The average intensity emitted by the patch of INK2 was obtained from stored bitmap images and can be represented, with reference of FORMULATION B at 100%, as follows:

| INK1 blank formulation | Cascade efficiency |
|---|---|
| Formulation A (solvent-based) | 152% |
| Formulation B (UV-curable) | 100% |

This example demonstrates that the cascade efficiency can be increased by more than 50% depending on the blank ink formulation of INK1, which comes from a larger amount of the phosphorescent pigment being available at the interface to the layer formed from INK2.

Formulation Blank A (Solvent Based):
21.3% NeoCryl B-728, 51.6% Butylglycol acetate, 21.7% Ethyl-3 ethoxypropionate, 0.3% Aerosil 200, 1.3% Byk-053 (anti-foam agent), 3.5% Dowanol DPM, 0.3% BYK-D410. (surfactant)

Formulation Blank B (UV-Curable):
31.5 wt.-% Tripropyleneglycol diacrylate monomer. 17.9 wt.-% trimethylolpropane triacrylate, 19.0 wt.-% EBECRYL™ 2959, 11.6 wt.-% EBECRYL™ 80, 2.1 wt.-% Airex 900, 1.0 wt.-% GENORAD™ 20, 9.5 wt.-% Calcium carbonate, 2.1 wt.-% Benzil dimethyl ketal and 5.3 wt.-% IRGACURE® 1173.

Formulation C (Digital Ink):
87%-weight Methylethylketone, 10.3%-weight of a hydroxyl-containing copolymer made from 84%-weight vinyl chloride and 16%-weight of acrylic acid ester (commercially available from Wacker Chemie under the tradename VINNOL E15/40 A) and 2%-weight of a terpolymer made from 84%-weight vinyl chloride, 15%-weight vinyl acetate and 1%-weight dicarboxylic acid (commercially available from Wacker Chemie under the trade name VINNOL E15/45 M).

The invention claimed is:

1. A security element comprising a first material MAT1 and a second material MAT2, which are formed in or on a substrate, in such a manner that areas occupied by MAT1 and MAT2 overlap partially or fully so that there are three areas recognizable: an area wherein MAT1, but not MAT2 is provided, an area wherein MAT2, but no MAT1 is provided, and an area wherein both MAT1 and MAT2 are provided,
   the first material MAT1 comprising a phosphorescent pigment (donor),
   the second material MAT2 comprising a fluorescent dye or pigment (acceptor),
   wherein the phosphorescent pigment present in MAT1 emits phosphorescence radiation in at least one first phosphorescence emission wavelength range $\lambda_{1e}$ upon excitation by electromagnetic radiation falling within a phosphorescence excitation wavelength range $\lambda_{1a}$, and
   the fluorescent dye or pigment present in MAT2 emits fluorescence radiation in at least one second fluorescence emission wavelength range $\lambda_{2e}$ upon excitation by electromagnetic radiation falling within an fluorescence excitation wavelength range $\lambda_{2a}$ of the fluorescent dye or pigment, and
   said first phosphorescence emission wavelength range $\lambda_{1e}$ of the phosphorescent pigment present in MAT1 overlaps with the excitation wavelength range $\lambda_{2a}$ of the fluorescent dye or pigment present in MAT2, so that after irradiation of the security element with electromagnetic radiation within the phosphorescence excitation wavelength range $\lambda_{1a}$, the emission of fluorescence radiation in the emission wavelength range $\lambda_{2e}$ is observable.

2. The security element according to claim 1, wherein MAT1 is an ink applicable by gravure printing, offset printing, intaglio printing, pad printing, flexographic printing or screen printing, and MAT2 is an ink applicable by inkjet printing.

3. The security element according to claim 1, wherein MAT2 is comprised in a digital code, such as a QR code, dot-matrix code or bar code.

4. The security element according to claim 1, wherein MAT2 is comprised in a serial code or product code, or wherein MAT2 is item-specific.

5. The security element according to claim 1, wherein MAT1 and MAT2 are present in the form of layers on a substrate, and MAT2 is provided directly on MAT1, or wherein MAT1 is provided directly on MAT2.

6. The security element according to claim 1, wherein MAT1 is comprised in the substrate and MAT2 is provided directly on the substrate, or wherein MAT2 is comprised in the substrate and MAT1 is provided directly on the substrate.

7. The security element according to claim 6, wherein the substrate comprising MAT1 or MAT2 is selected from one or more of glass, ceramics, plastics, paper, and cardboard.

8. The security element according to claim 1, wherein one or both of MAT1 and MAT2 is/are not visually distinguishable from the substrate by the naked eye.

9. The security element according to claim 1, wherein one or both of MAT1 and MAT2 is/are provided in the form of a pattern, indicia, symbol or logo.

10. The security element according to claim 9, wherein MAT1 is provided in the form of a pattern, indicia, symbol or logo, and wherein MAT2 is provided in the form of a code, which may or may not be item-specific.

11. The security element according to claim 1, wherein the area wherein MAT1 is provided entirely includes the area wherein MAT2 is provided.

12. The security element according to claim 1, wherein $\lambda_{1a\text{-}max} < \lambda_{1e\text{-}max} < \lambda_{2e\text{-}max}$, wherein $\lambda_{1a\text{-}max}$, $\lambda_{1e\text{-}max}$, and $\lambda_{2e\text{-}max}$ denote the wavelengths of the excitation and emission peaks in the respective excitation and emission wavelength regions of the phosphorescent pigment present in MAT1 and the fluorescent dye or pigment present in MAT2.

13. A method for authenticating a security element as defined in claim 1, which comprises the steps
  i. irradiating the security element with a light source in the wavelength range $\lambda_{1a}$ for a given time to excite the phosphorescent pigment in MAT1 to emit phosphorescence radiation in the wavelength range $\lambda_{1e}$;
  ii. after the given time has elapsed, subsequently detecting a response emitted by a region of a spatial overlap of the security element within the wavelength range $\lambda_{2e}$ and
  iii. judging the authenticity of the security element on the basis of the response in the wavelength range $\lambda_{2e}$.

14. The authentication method according to claim 13, wherein step iii. comprises a sub-step iii.a of extracting a value related to at least one parameter associated with the emission in the wavelength region $\lambda_{2e}$ and a sub-step iii.b of determining whether the extracted value corresponds within a certain level of confidence to a value that is characteristic for an authentic security element.

15. The authentication method according to claim 14, wherein the parameter is associated with the intensity of the observed emission in the wavelength region $\lambda_{2e}$.

16. The authentication method according to claim 15, wherein the parameter is associated with the decay time of the phosphorescent pigment.

17. The authentication method according to claim 13, wherein the method additionally comprises steps for acquiring an image of the security element in the wavelength range $\lambda_{2e}$ upon illumination in the wavelength range $\lambda_{2a}$, and processing the acquired image.

18. The authentication method according to claim 16, which further comprises generating a digital correlation mask from said image.

19. An authentication apparatus for authenticating a security element, wherein the security element comprises a first material MAT1 and a second material MAT2 formed in or on a substrate, in such a manner that areas occupied by MAT1 and MAT2 overlap partially or fully so that there are three areas recognizable: an area wherein MAT1, but not MAT2 is provided, an area wherein MAT2, but no MAT1 is provided, and an area wherein both MAT1 and MAT2 are provided,
  the first material MAT1 comprising a phosphorescent pigment (donor),
  the second material MAT2 comprising a fluorescent dye or pigment (acceptor),
  wherein the phosphorescent pigment present in MAT1 emits phosphorescence radiation in at least one first phosphorescence emission wavelength range $\lambda_{1e}$ upon excitation by electromagnetic radiation falling within a phosphorescence excitation wavelength range $\lambda_{1a}$, and
  the fluorescent dye or pigment present in MAT2 emits fluorescence radiation in at least one second fluorescence emission wavelength range $\lambda_{2e}$ upon excitation by electromagnetic radiation falling within an fluorescence excitation wavelength range $\lambda_{2a}$ of the fluorescent dye or pigment, and
  said first phosphorescence emission wavelength range $\lambda_{1e}$ of the phosphorescent pigment present in MAT1 overlaps with the excitation wavelength range $\lambda_{2a}$ of the fluorescent dye or pigment present in MAT2, so that after irradiation of the security element with electromagnetic radiation within the phosphorescence excitation wavelength range $\lambda_{1a}$, the emission of fluorescence radiation in the emission wavelength range $\lambda_{2e}$ is observable, and the security element is authenticated with the method described in claim 13, wherein the apparatus comprises a radiation source for performing step i, a detector for performing step ii and a processing unit for performing step iii.

20. The authentication apparatus according to claim 19, comprising
  a first radiation source for emitting substantially in the wavelength range $\lambda_{1a}$ for irradiating the phosphorescent pigment in MAT1;
  an imager selectively sensitive in the wavelength range $\lambda_{2e}$ for capturing images of the security element;
  a computing device for storing and processing the captured images under the first radiation source and for comparing the processed image result with a set of predefined stored rules to judge whether the security element is authentic.

21. The authentication apparatus according to claim 19, further comprising a second light source emitting substantially in the wavelength range $\lambda_{2a}$ for irradiating the fluorescent dye or pigment in MAT2.

22. The authentication apparatus according to claim 19, wherein said computing device is furthermore arranged for decoding information in a digital code.

23. A commercial good of value or security document comprising the security element according to claim 1.

24. A process for producing a security element according to claim 1, which comprises
  providing a first material MAT1 and a second material MAT2 in or on a substrate, in such a manner that the areas occupied by MAT1 and MAT2 overlap fully or partially so that there are three areas recognizable: an area wherein MAT1, but not MAT2 is provided, an area wherein MAT2, but no MAT1 is provided, and an area wherein both MAT1 and MAT2 are provided, the first material MAT1 comprising a phosphorescent pigment (donor), the second material MAT2 comprising a fluorescent dye or pigment (acceptor), wherein the phosphorescent pigment present in MAT1 emits phosphorescence radiation in at least one first phosphorescence emission wavelength range $\lambda_{1e}$ upon excitation by electromagnetic radiation falling within a phosphorescence excitation wavelength range $\lambda_{1a}$, and the fluorescent dye or pigment present in MAT2 emits fluorescence radiation in at least one second fluorescence emission wavelength range $\lambda_{2e}$ upon excitation by electromagnetic radiation falling within an fluorescence excitation wavelength range $\lambda_{2a}$ of the fluorescent dye or pigment, and said first phosphorescence emission wavelength range $\lambda_{1e}$ of the phosphorescent pigment present in MAT1 overlaps with the excitation wavelength range $\lambda_{2a}$ of the fluorescent dye or pigment present in MAT2, so that after irradiation of the security element with electromagnetic radiation within the phosphorescence excitation wavelength range $\lambda_{1a}$, the emission of fluorescence radiation in the emission wavelength range $\lambda_{2e}$ is observed.

* * * * *